United States Patent
Goto et al.

(10) Patent No.: US 7,876,874 B2
(45) Date of Patent: Jan. 25, 2011

(54) RADIOGRAPHING APPARATUS AND IMAGE PROCESSING PROGRAM

(75) Inventors: Taiga Goto, Kashiwa (JP); Osamu Miyazaki, Moriya (JP); Koichi Hirokawa, Kashiwa (JP); Yasuo Omi, Nagareyama (JP)

(73) Assignee: Hitachi Medical Corporation, Tokyo (JP)

( * ) Notice: Subject to any disclaimer, the term of this patent is extended or adjusted under 35 U.S.C. 154(b) by 169 days.

(21) Appl. No.: 11/914,520

(22) PCT Filed: May 12, 2006

(86) PCT No.: PCT/JP2006/309551

§ 371 (c)(1),
(2), (4) Date: Dec. 10, 2008

(87) PCT Pub. No.: WO2006/123581

PCT Pub. Date: Nov. 23, 2006

(65) Prior Publication Data

US 2009/0147919 A1 Jun. 11, 2009

(30) Foreign Application Priority Data

May 18, 2005 (JP) .............................. 2005-145166
Aug. 10, 2005 (JP) .............................. 2005-232060

(51) Int. Cl.
*G01N 23/087* (2006.01)
(52) U.S. Cl. ...................... 378/5; 378/98.11; 378/98.12
(58) Field of Classification Search ..................... 378/5, 378/98.9, 98.11, 98.12
See application file for complete search history.

(56) References Cited

U.S. PATENT DOCUMENTS

| 5,570,403 | A | * | 10/1996 | Yamazaki et al. | ............... 378/5 |
| 6,661,873 | B2 | * | 12/2003 | Jabri et al. | ............... 378/98.11 |
| 6,816,564 | B2 | * | 11/2004 | Charles et al. | ............... 378/5 |
| 6,922,462 | B2 | * | 7/2005 | Acharya et al. | ............ 378/98.11 |
| 7,272,429 | B2 | * | 9/2007 | Walker et al. | ............... 600/407 |

(Continued)

FOREIGN PATENT DOCUMENTS

EP 1387320 A2 2/2004

(Continued)

OTHER PUBLICATIONS

English translation of the International Preliminary Report On Patentability (including English translation of the Written Opinion) in connection with International Application No. PCT/JP2006/309551.

(Continued)

*Primary Examiner*—Edward J Glick
*Assistant Examiner*—Thomas R Artman
(74) *Attorney, Agent, or Firm*—Cooper & Dunham LLP

(57) ABSTRACT

A radiographing apparatus according to an aspect of the present invention is characterized in that an image processing device comprises an acquisition device which acquires projection data of a first energy spectrum and projection data of a second energy spectrum, and a synthetic image generating device which synthesizes a first image on the basis of the projection data of the first energy spectrum, and a second image on the basis of the projection data of the second energy spectrum according to a predetermined synthetic condition, and generating a synthetic image, and a display device displays the generated synthetic image.

20 Claims, 25 Drawing Sheets

U.S. PATENT DOCUMENTS

| | | | |
|---|---|---|---|
| 7,756,240 B2 * | 7/2010 | Nishide et al. | 378/5 |
| 2004/0022359 A1 | 2/2004 | Acharya et al. | |
| 2004/0077088 A1 | 4/2004 | Seppi et al. | |
| 2004/0102688 A1 | 5/2004 | Walker et al. | |
| 2005/0084060 A1 | 4/2005 | Charles, Jr. et al. | |
| 2008/0013819 A1 * | 1/2008 | Eilbert et al. | 382/141 |

FOREIGN PATENT DOCUMENTS

| | | |
|---|---|---|
| JP | 2003-180669 | 7/2003 |
| JP | 2004-188187 | 7/2004 |

OTHER PUBLICATIONS

Apr. 1, 2010 European search report in connection with a counterpart European patent application No. EPA-44712.

European Patent Office communication in connection with European patent application No. 06 732 532.4.

* cited by examiner

| IRRADIATION POSITION | X-RAY EFFECTIVE ENERGY |
|---|---|
| ○ | LOW |
| △ | MIDDLE |
| □ | HIGH |

FIG.27
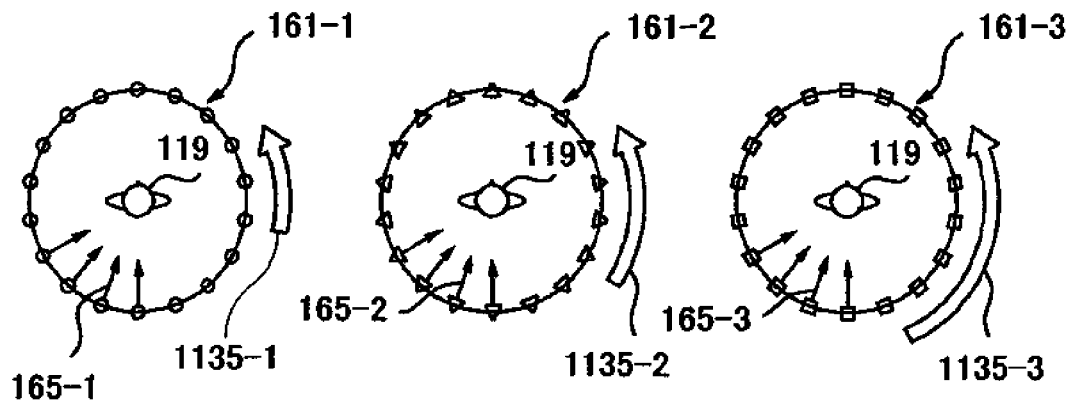
FIG.28
| IRRADIATION POSITION | X-RAY EFFECTIVE ENERGY | SCANNING SPEED |
|---|---|---|
| ○ | LOW | SMALL |
| △ | MIDDLE | MIDDLE |
| □ | HIGH | LARGE |
FIG.29
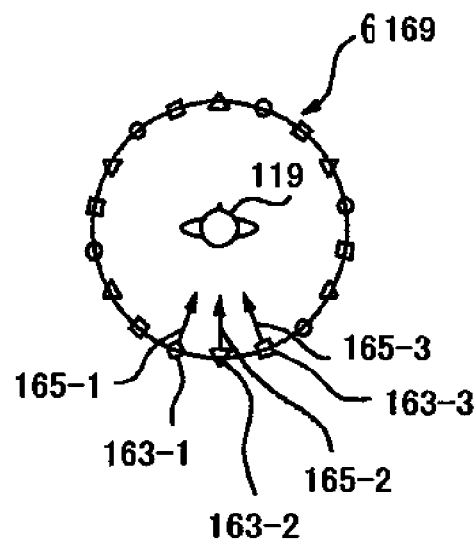

| IRRADIATION POSITION | X-RAY EFFECTIVE ENERGY | X-RAY TUBE CURRENT |
|---|---|---|
| ○ | LOW | LARGE |
| △ | MIDDLE | MIDDLE |
| □ | HIGH | SMALL |

| IRRADIATION POSITION | X-RAY EFFECTIVE ENERGY | NUMBER OF VIEWS |
|---|---|---|
| ○ | LOW | LARGE |
| △ | MIDDLE | MIDDLE |
| □ | HIGH | SMALL |

RADIOGRAPHING APPARATUS AND IMAGE PROCESSING PROGRAM

TECHNICAL FIELD

The present invention relates to a radiographing apparatus and an image processing program, and in particular, to a useful technique to generate a more highly detailed tomogram from data acquired using a plurality of X-ray energies.

This application is an application with a claim of priority under the Paris Convention on the basis of Japanese Patent Application No. 2005-145166 and Japanese Patent Application No. 2005-232060 under the Japanese Patent Law, and an application incorporating Japanese Patent Application No. 2005-145166 and Japanese Patent Application No. 2005-232060 by reference in order to enjoy the benefit of them.

BACKGROUND ART

In a Patent Document 1, a multi-energy CT which radiates two kinds of X-rays which have different energy spectra is disclosed. When X-rays with a spectral band width transmit an object to be examined, since many X-rays in low energy are absorbed, a so-called beam hardening effect that an energy peak value shifts to a high side arises. It is known that the beam hardening effect causes artifact generation and accuracy deterioration of a CT value. In the multi-energy CT, it is considered that it is possible to reduce the artifact resulting from the beam hardening because good beam hardening compensation becomes possible using data acquired with two kinds of energy spectra, and hence, precision improvement of a CT value is expected.

In addition, in the multi-energy CT, it is considered that generation of an image which expresses an atomic number and a density is possible because it is possible to obtain data which expresses different attenuations from a Compton effect and a photoelectric effect, applications such as separation of a bone and a contrasted blood vessel, which is difficult in CT of a type which radiates one kind of energy spectrum, are expected.

Patent Document 1: Japanese Patent Application Laid-Open No. 2004-188187

DISCLOSURE OF THE INVENTION

In a case of CT which is not monochrome and which uses X-rays with a spectral band width, various artifacts such as shading and streak arise by the beam hardening effect. In addition, since an X-ray with only one kind of energy spectrum is used, there is a limit in correction accuracy of the beam hardening effect. In the CT by monochromatic radiation light, since a phenomenon of the beam hardening does not arise, it is hard to generate the artifact, and there are advantages in respect of CT value accuracy and image contrast.

However, since an apparatus, which is expensive and huge, such as a cyclotron is necessary to generate a monochromatic X-ray, it is hard to use it for clinical widely, and its application is limited in a restrictive range. In multi-energy CT, applications such as effective compensation of the beam hardening effect, and separation of a bone and a contrasted blood vessel from data obtained from a plurality of energy spectra are expected. However, sufficient analyses are not made about other applications, in particular, an attempt of enhancing image contrast.

An object of the present invention is to provide a radiographing apparatus and an image processing program which can generate a tomogram, which is more highly detailed and excellent in contrast, from data acquired using a plurality of energy spectra.

In order to solve the above-mentioned issues, a radiographing apparatus which relates to the present invention is a radiographing apparatus comprising an X-ray source which radiates an X-ray with a first energy spectrum, and an X-ray with a second energy spectrum, an X-ray detector which detects the X-ray with the first energy spectrum and the X-ray with the second energy spectrum which transmit an object to be examined, and outputs projection data of the first energy spectrum, and projection data of the second energy spectrum, a control device which controls operations of the X-ray source and the X-ray detector, an image processing device which generates a desired image on the basis of the projection data of the first energy spectrum and the projection data of the second energy spectrum, and a display device which displays the image, wherein the image processing device comprises an acquisition device which acquires the projection data of the first energy spectrum and the projection data of the second energy spectrum, and a synthetic image generating device which synthesizes a first image on the basis of the projection data of the first energy spectrum, and a second image on the basis of the projection data of the second energy spectrum according to a predetermined synthetic condition to generate a synthetic image, and wherein the display device displays the generated synthetic image.

In addition, an image processing program which relates to the present invention is characterized by making a computer execute a reading step of reading projection data of an X-ray with a first energy spectrum and projection data of an X-ray with a second energy spectrum which transmit an object to be examined, and a synthesizing step of synthesizing a first image on the basis of the projection data of the first energy spectrum, and a second image on the basis of the projection data of the second energy spectrum according to a predetermined synthetic condition, and generating a synthetic image.

Here, the "first image on the basis of the projection data of the first energy spectrum" includes a profile view which is projection data of the first energy spectrum, and a reconstructed image obtained by reconstructing this projection data (that is, profile view). Similarly, the "second image on the basis of the projection data of the second energy spectrum" includes a profile view which is projection data of the second energy spectrum, and a reconstructed image obtained by reconstructing this projection data (that is, profile view).

In addition, cases of defining the "first energy spectrum" and the "second energy spectrum" include not only a case of defining an energy spectrum using at least one of characteristic quantities, such as a shape, an area, a wave height, maximum energy, and minimum energy of the energy spectrum of X-rays, but also a case of defining an energy spectrum using effective energy corresponding to the energy spectrum. Furthermore, the cases of defining the "first energy spectrum" and the "second energy spectrum" include also a case of being sufficient just to distinguish them from other energy spectra, and giving a definition by only performing labeling (for example, a first one, a second one, and the like) without using the above-mentioned characteristic quantities and effective energy.

According to the present invention, in X-ray computerized tomography, there is an effect that it is possible to generate a tomogram which is more highly detailed and excellent in contrast from data acquired using a plurality of energy spectra.

BRIEF DESCRIPTION OF THE DRAWINGS

FIG. 27 is a diagram illustrating control of scanning speed according to the X-ray effective energy;

FIG. 28 is a relational diagram among the irradiation position, the X-ray effective energy, and the scanning speed in FIG. 27;

FIG. 29 is a diagram illustrating control of the X-ray tube current according to the X-ray effective energy;

DESCRIPTION OF SYMBOLS

Figure 1:
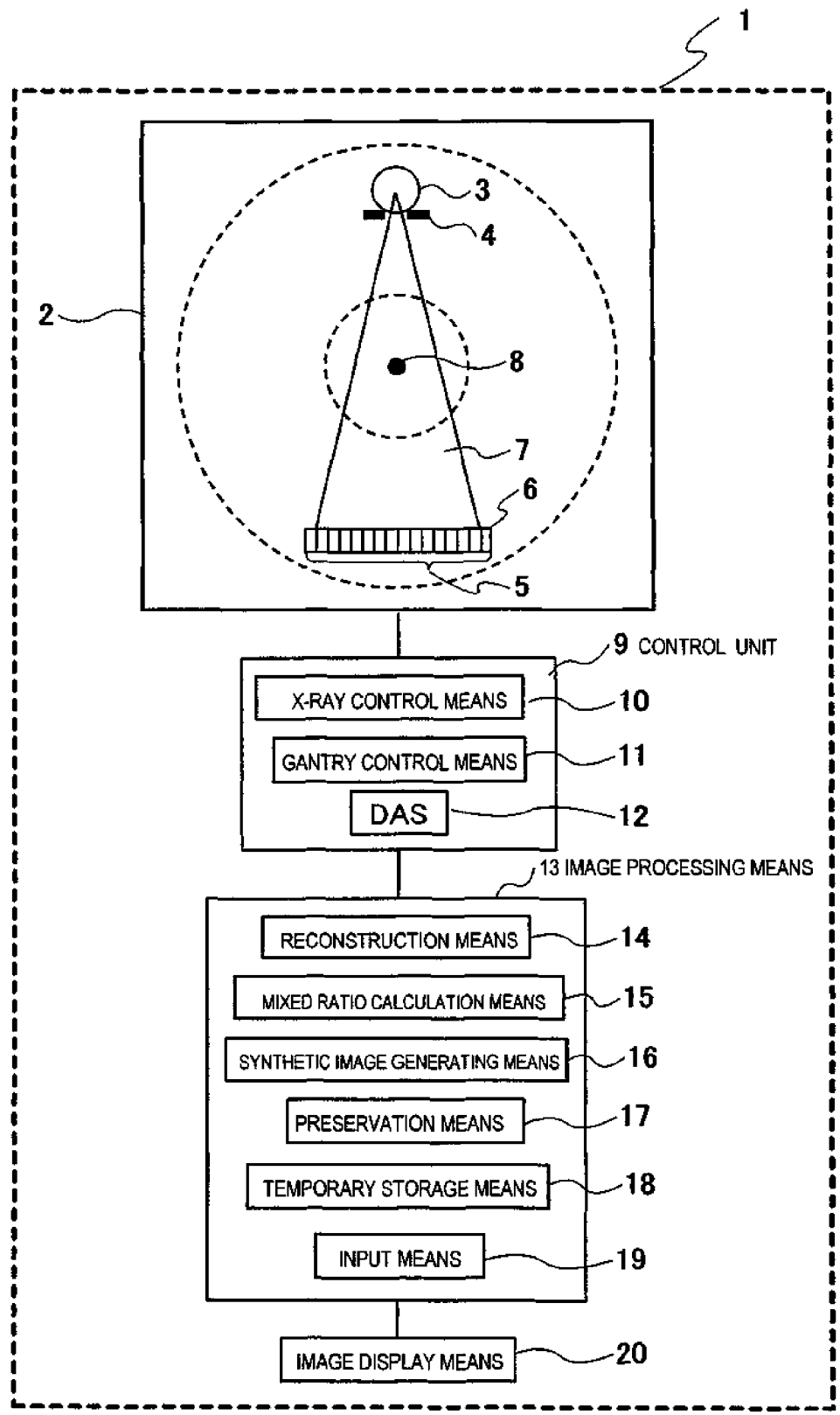
FIG. 1 is a structural diagram of an X-ray CT scanner of the present invention.

1 . . . X-ray CT scanner
2 . . . Gantry
3 . . . X-ray source
4 . . . Collimator
5 . . . Detector array
6 . . . Detector element
7 . . . X-ray
8 . . . Rotation center
9 . . . Control unit
10 . . . X-ray control means
11 . . . Gantry control means
12 . . . DAS
13 . . . Image processing means
14 . . . Reconstruction means
15 . . . Mixed ratio calculation means
16 . . . Synthetic image generating means
17 . . . Preservation means
18 . . . Temporary storage means
19 . . . Input means
20 . . . Image display means
100 . . . X-ray CT scanner
103 . . . Scanner unit
105 . . . Image processing unit
107 . . . X-ray tube assembly
119 . . . Object to be examined
127 . . . X-ray detector
137 . . . Control unit
139 . . . Memory storage
141 . . . Display unit
145 . . . Input-output unit
149 . . . Photon energy
151 . . . Energy intensity 153, 155, 157 . . . Energy curves
161, 169 . . . Scan (Radiographing)
163 . . . Irradiation position
165 . . . X-ray
167 . . . Image
174 . . . Color
175 . . . Monochrome color image
177 . . . Synthetic color image
183 . . . Processed image
185 . . . Difference image
187 . . . Differential monochrome color image
189 . . . Differential synthetic color image
191 . . . Emphasized image
193, 199 . . . Projection data
195 . . . Image reconstruction calculation
197, 1101 . . . Reconstructed image data
1107, 1120 . . . Curves (X-ray absorption coefficients)
1115, 1127 . . . Errors
1129, 1131, 1133 . . . Filters
1135 . . . Scanning speed
1137, 1137a, 1137b . . . . Targets (Anodes)
1138 . . . Collision surface
1139 . . . Electron gun (Cathode)
1141 . . . Deflector
1143 . . . Electron ray
1145 . . . X-ray
1149, 1151 . . . Energy curves
1157 . . . X-ray
1159 . . . Projection data

BEST MODE FOR CARRYING OUT THE INVENTION

Hereafter, preferable embodiments of an X-ray CT scanner which relates to the present invention will be described in detail according to accompanying drawings.

Embodiment 1

FIG. 1 is a diagram illustrating a preferable embodiment of a radiographing apparatus (hereafter, this is abbreviated as an "X-ray CT scanner") which relates to the present invention. An X-ray CT scanner 1 which relates to the present invention includes a gantry 2, and the gantry 2 has an X-ray source 3, a collimator 4, and a detector array 5 which are located on counter faces of the gantry 2. The detector array 5 is formed of detector elements 6 which detect X-rays which transmit an object to be examined on a bed which is not illustrated. The detector elements 6 are arranged in a form of a transverse row, or a form of a plurality of parallel transverse rows. Each of the detector elements 6 generates an electric signal expressing strength of an incident X-ray beam, in other words, attenuation at the time of the X-ray beam transmitting an object to be examined. X-ray projection data is acquired by the gantry 2 rotating with centering on a rotation center 8 in a state that an X-ray 7 is radiated from the X-ray source 3. The gantry 2 and X-ray source 3 are controlled by a control unit 9 of the X-ray CT scanner. The control unit 9 includes X-ray control means 10, gantry control means 11, and a DAS (data acquisition system) 12, and an analog signal from the detector element 6 is converted into a digital signal by the DAS 12. The digitized X-ray data is reconstructed by reconstruction means 14 in image processing means 13, and is stored in preservation means in the image processing means 13. The image processing means 13 is a processing unit such as a computer, and is constructed of mixed ratio calculation means 15 of calculating a mixing ratio of reconstructed images in respective energy spectra, synthetic image generating means 16 of generating a synthetic image on the basis of the mixed ratio calculated by the mixed ratio calculation means, preservation means 17 such as a hard disk, temporary storage means 18 such as memory, and input means 19 such as a mouse and a keyboard. In addition, it includes at least one of a Digital Signal Processor (DSP), a Micro Processor Unit (MPU), and a Central Processing Unit (CPU) which are not illustrated. The image display means 20 is a display apparatus, which is united with or is independent from the image processing means 13, such as a display unit. Although the control unit 9 and the data processing means 13 are separated in FIG. 1, both may be unified. In addition, the reconstruction means 14 may be independent from the image processing means 13.

Figure 2:
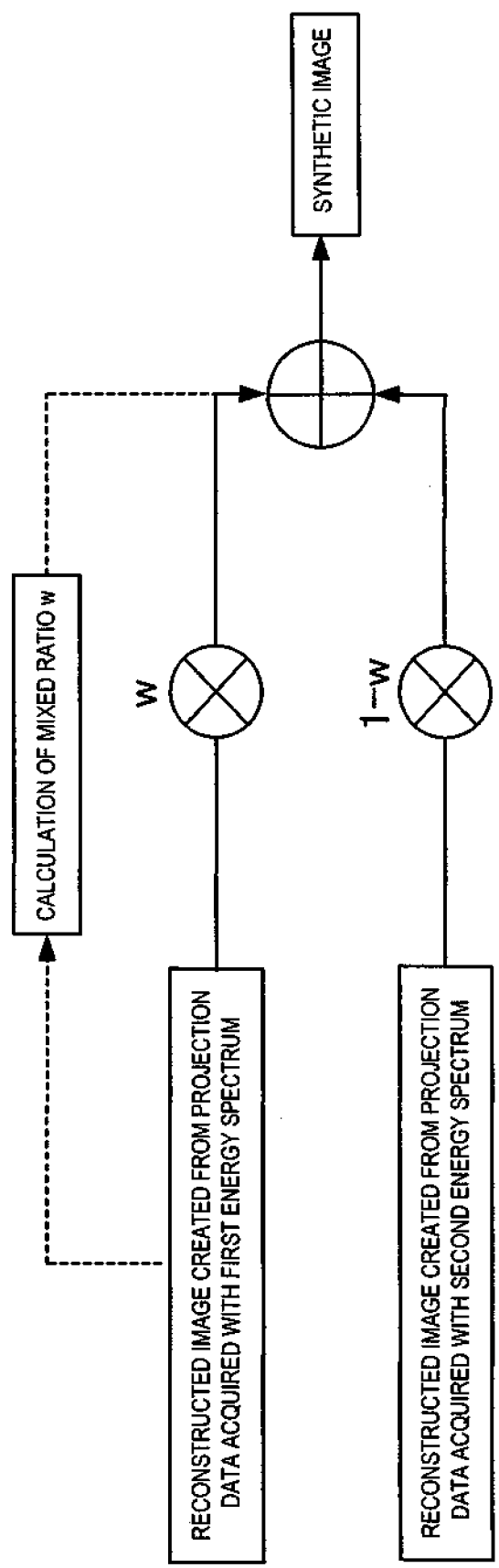
FIG. 2 is an explanatory diagram of a method of generating a synthetic image from a reconstructed image generated from projection data acquired in a plurality of energy spectra.

FIG. 2 is a schematic diagram illustrating a method of generating a synthetic image from a reconstructed image, generated from projection data which is acquired in a plurality of energy spectra, in the embodiment of the X-ray CT scanner 1 which relates to the present invention. A mixed ratio is calculated by on the basis of a reconstructed image generated from projection data acquired in a first energy spectrum (hereinafter, the "first reconstructed image"), and a reconstructed image generated from projection data acquired in a second energy spectrum (hereinafter, the "second reconstructed image"), and a synthetic image is generated on the basis of this mixed ratio. In FIG. 2, a mixed ratio w is calculated from the first reconstructed image, and the first reconstructed image is mixed at a mixed ratio w, and the second reconstructed image is mixed at a ratio of (1−w). In the above, although the mixed ratio is calculated from the first reconstructed image, the mixed ratio may be calculated from the second reconstructed image, or may be calculated from both of reconstructed images. Although an example of acquiring projection data in two energy spectra in FIG. 2 is illustrated for simplicity, it is also sufficient to perform acquisition in three or more energy spectra.

Figure 3:
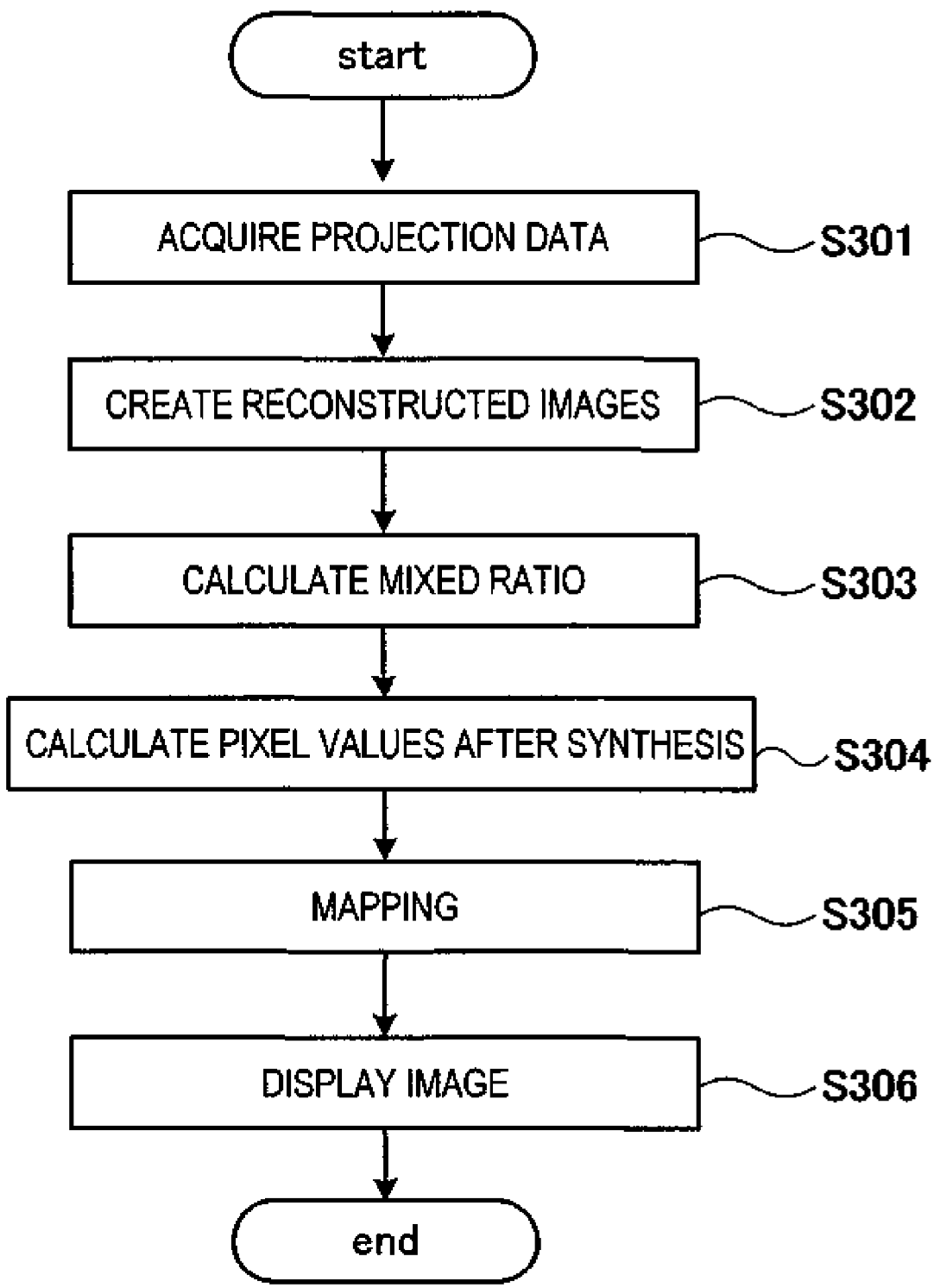
FIG. 3 is a flowchart illustrating a process flow of a first embodiment.

FIG. 3 is a process flow from projection data acquisition to synthetic image display in the first embodiment of the X-ray CT scanner which relates to the present invention.

At step S301 projection data is acquired first (S301). The X-ray CT scanner 1 is a multi-energy system of CT scanner, and multiple times of scans which operate at a plurality of potentials such as 80 kVp and 120 kVp is executed in a continuous system or an interleaving system for projection data to be acquired. Alternatively, it is made that a special filter is arranged between the X-ray source 3 and the detector elements 6, and various detector rows acquire projection data in various energy spectra. Alternatively, the multi-energy system of CT scanner may be achieved by using an energy sensing type detector.

At step S302, the reconstruction means 14 generates reconstructed images about projection data in the respective energy spectra (S302). The DAS 12 acquires X-ray projection data in the first energy spectrum (hereinafter, the "first projection data") and X-ray projection data in the second energy spectrum (hereinafter, the "second projection data") that the detector array 5 detects, and sends them out to the image processing means 13. The image processing means 13 acquires the first projection data and the second projection data, and the reconstruction means 14 generates the first reconstructed image on the basis of the first projection data. Similarly, the second reconstructed image is generated on the basis of the second projection data.

At step S303, the mixed ratio calculation means 15 calculates a mixed ratio (S303). A calculation method of the mixed ratio will be mentioned later.

At step S304, the synthetic image generating means 16 calculates pixel values after synthesis on the basis of the mixed ratio which is obtained (S304). The pixel values after synthesis are calculated according to the following formula 1.

[Formula 1]

$$OIMG = w \cdot IMG_1 + (1-w) \cdot IMG_2 \quad (1)$$

Here, OIMG denotes a synthetic image, IMG1 denotes a pixel value in the first reconstructed image generated from the projection data acquired in the first energy spectrum, IMG2 denotes a pixel value in the second reconstructed image generated from the projection data acquired in the second energy spectrum, and w denotes a mixed ratio, respectively. In addition, w is a real number between 0 and 1. S303 to 304 are repeated every pixel or every local area.

At step S305, the synthetic image generating means 16 generates a synthetic image by mapping the pixel values after the synthesis in the respective pixels or the respective local areas which are calculated (S305).

At step S306, the image display means 20 displays the synthetic image which is generated (S306).

Figure 4:
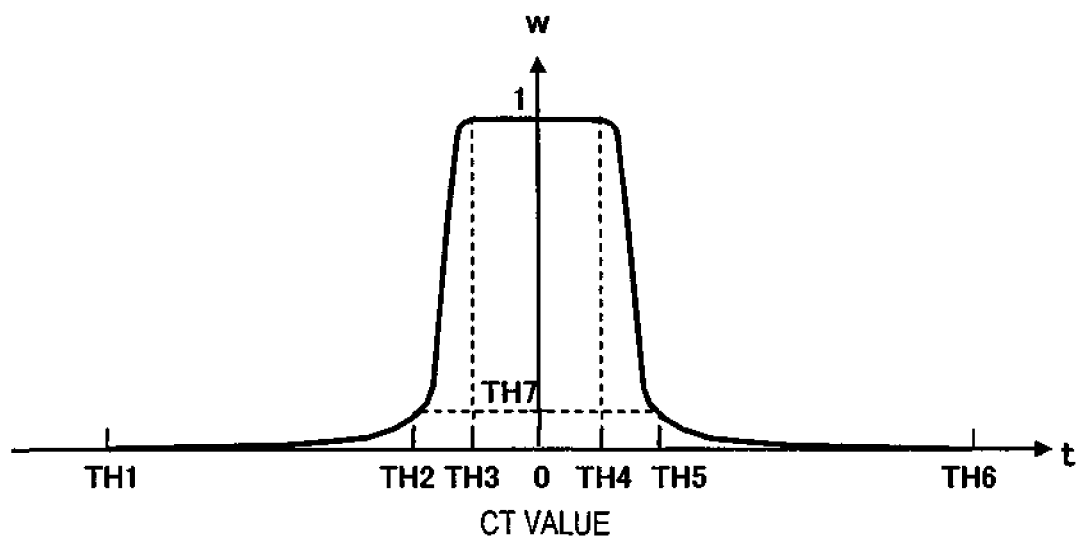
FIG. 4 is an explanatory diagram of a determination method of a mixing ratio in the first embodiment.

Next, a calculation method of the mixed ratio in the first embodiment of the X-ray CT scanner which relates to the present invention will be described. A CT value has a value which is generally different every tissue. For example, a bone has a CT value of about 1000 HU, organs such as a liver and a brain have about 25 to 80 HU, fat has about −100 HU, and a lung field has about −800 HU. It is known that the lower energy of the X-rays radiated is, the more organs such as a brain tend to absorb X-rays, and the higher energy of the X-rays radiated is, the more bones tend to absorb X-rays. Here, when effective energy of the first energy spectrum is set low and effective energy of the second energy spectrum is set high, a synthetic image with good contrast can be obtained by strengthening a component of the reconstructed image generated from the projection data acquired in the first energy spectrum in a site with the tendency that the lower energy is, the more it absorbs X-rays, strengthening a component of the reconstructed image generated from the projection data acquired in the second energy spectrum in a site with the tendency that the higher energy is, the more it absorbs X-rays, and mixing them. Thus, what is necessary is to set the mixed ratio and to generate a synthetic image as illustrated in FIG. 4, for example. The graph in FIG. 4 is expressed in the following formula 2.

[Formula 2]

$$\begin{cases} t \leq TH1 & w = 0 \\ TH1 \leq t \leq TH2 & w = \dfrac{TH7}{(TH2-TH1)^2} \cdot (t-TH1)^2 \\ TH2 \leq t \leq TH3 & w = \sin\left(\dfrac{\pi}{2(TH3-TH2)} \cdot (t-TH2)\right) \\ TH3 \leq t \leq TH4 & w = 1 \\ TH4 \leq t \leq TH5 & w = \cos\left(\dfrac{\pi}{2(TH5-TH4)} \cdot (t-TH4)\right) \\ TH5 \leq t \leq TH6 & w = \dfrac{TH7}{(TH5-TH6)^2} \cdot (t-TH6)^2 \\ TH6 \leq t & w = 0 \end{cases} \quad (2)$$

Here, it is desirable that TH1 is about −1000, TH2 is about −200, TH3 is about −100, TH4 is about +80, TH5 is about +160, TH6 is about +1000, and TH7 is about 0.1. The mixed ratio is not limited to the example illustrated in FIG. 4 and formula 2, but an arbitrary curve shape and a formula may be sufficient so long as it is such a mixed ratio that strengthens a component of the first reconstructed image generated from the first projection data acquired in the first energy spectrum in a site with the tendency that the lower energy is, the more it absorbs X-rays, and strengthens a component of the second reconstructed image generated from the second projection data acquired in the second energy spectrum in a site with the tendency that the higher energy is, the more it absorbs X-rays.

According to this embodiment, it is possible to heighten the mixed ratio of a reconstructed image with higher contrast every pixel or every local area between the first reconstructed image and the second reconstructed image, and to generate a synthetic image.

In addition, in the above-mentioned embodiment, although the mixed ratio is calculated at S303 after the first reconstructed image and the second reconstructed image are generated at S302, and the pixel values are calculated at S304 by synthesizing the first reconstructed image and the second reconstructed image, it is also sufficient to generate mixed projection data into which the first projection data and the second projection data are mixed according to a predetermined mixed ratio, and to generate a mixed synthetic image (reconstructed image) by reconstructing this mixed projection data. In this case, the mixed ratio is set so as to strengthen a component of the first projection data acquired in the first energy spectrum in a site with the tendency that the lower energy is, the more it absorbs X-rays, and to strengthen a component of the second projection data acquired in the second energy spectrum in a site with the tendency that the higher energy is, the more it absorbs X-rays.

Embodiment 2

Figure 5:
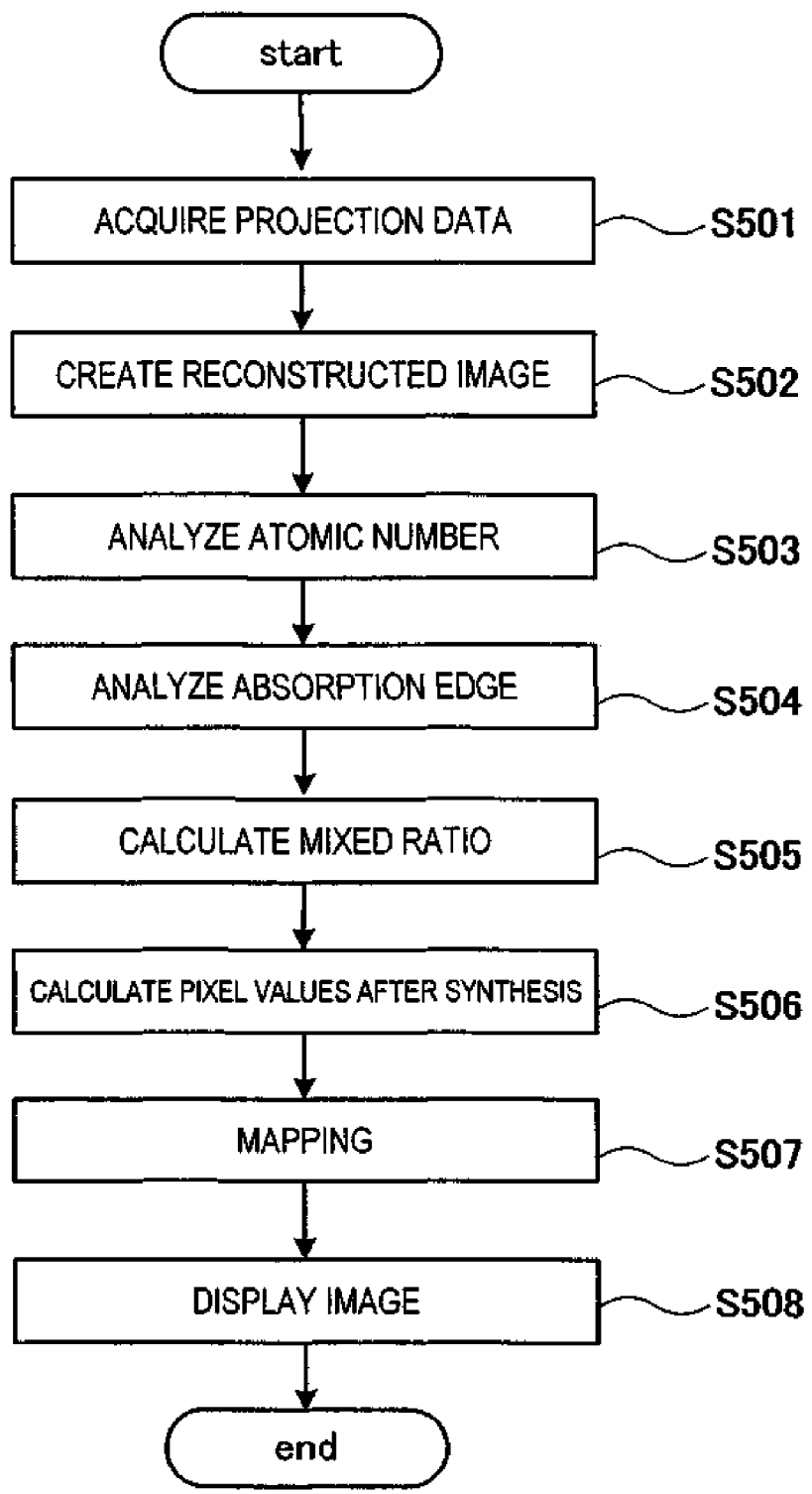
FIG. 5 is a flowchart illustrating a process flow of a second embodiment.

FIG. 5 is a process flow from projection data acquisition to synthetic image display in the second embodiment of the X-ray CT scanner which relates to the present invention.

At step S501 projection data is acquired first (S501). A method of data acquisition may be the same as that of the first embodiment.

At step S502, the reconstruction means 14 generates the first reconstructed image and the second reconstructed image about projection data in the respective energy spectra (S502).

At step S503, the mixed ratio calculation means 15 calculates an effectual atomic number in a noticed picture element or a local area (S503). The mixed ratio calculation means 15 segments the first reconstructed image and the second reconstructed image every tissue which has the same vital function (segmentation). Instead of obtaining a whole damping coefficient such as a conventional type CT, a multi-energy CT can obtain a pair of images which express different attenuations from Compton and photoelectric processing, and can obtain information on an effectual atomic number and a density. When using this property, it is possible to obtain an effectual atomic number every tissue, every noticed picture element, or every local area.

At step S504, the mixed ratio calculation means 15 obtains an X-ray absorption edge on the basis of the effectual atomic number obtained at S503 (S504). X-ray absorption characteristics are unique to a substance and an effectual atomic number and an X-ray absorption edge of a substance which is constructed of its atom keeps one-to-one correspondence. Therefore, when the effectual atomic number is known, it is possible to grasp the X-ray absorption edge corresponding to the substance. In order to complete S504 for a short time, it is desirable to generate a correspondence table of the substance and the X-ray absorption edge beforehand, and to refer to the table.

At step S505, the mixed ratio calculation means 15 calculates a mixed ratio (S505). A calculation method of the mixed ratio will be mentioned later.

At step S506, the synthetic image generating means 16 calculates pixel values after synthesis on the basis of the mixed ratio which is obtained at S505 (S506). A calculation method of the pixel values after synthesis may be the same as that of first embodiment. The synthetic image generating means 16 repeats S503 to S506 every pixel or every local area.

At step S507, the synthetic image generating means 16 generates a synthetic image by mapping the pixel values after the synthesis in the respective pixels or the respective local areas which are calculated at S506 (S507).

At step S508, the image display means 20 displays the synthetic image which is generated at S507 (S508).

Figure 6:
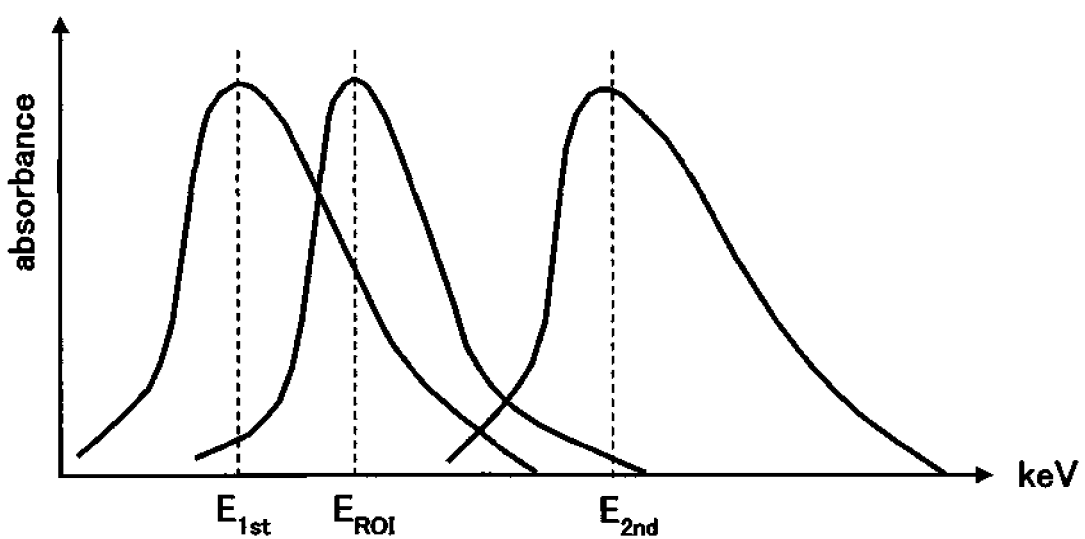
FIG. 6 is an explanatory diagram of a determination method of a mixing ratio in the second embodiment.

Next, the calculation method of the mixed ratio in the second embodiment of the X-ray CT scanner which relates to the present invention will be described with using FIG. 6. Here, a case that effective energy of the first energy spectrum is set low and effective energy of the second energy spectrum is set high will be described. Let the effective energy of the first energy spectrum be $E_{1st}$, and let the effective energy of the first energy spectrum be $E_{2nd}$. In addition, let an X-ray absorption edge of a substance in a noticed picture element or local area be $E_{ROI}$. The mixed ratio w is calculated with the following formula at this time.

[Formula 3]

$$\begin{cases} w = (1-t) \cdot E_{1st} + t \cdot E_{2nd} \\ t = \dfrac{E_{ROI} - E_{1st}}{E_{1st} + E_{2nd}} \end{cases} \quad (3)$$

In this embodiment, although the case that the effective energy of the first energy spectrum is set low and the effective energy of the second energy spectrum is set high is described, those skilled in the art can understand easily that it may be reverse to this.

Embodiment 3

Figure 7:
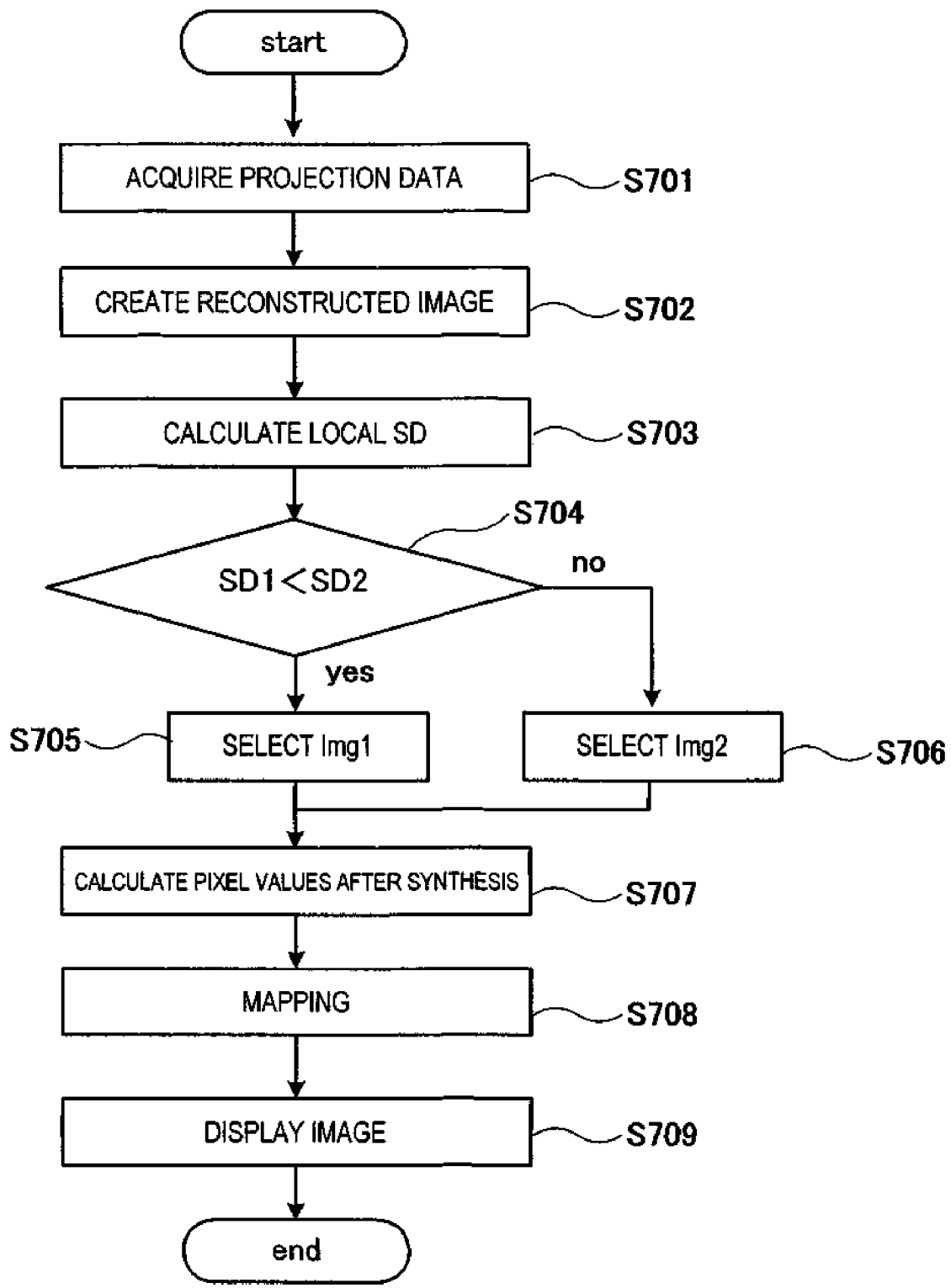
FIG. 7 is a flowchart illustrating a process flow of a third embodiment.

FIG. 7 is a process flow from projection data acquisition to synthetic image display in a third embodiment of the X-ray CT scanner which relates to the present invention.

At step S701, projection data is acquired first (S701). A method of data acquisition may be the same as those of the first embodiment and the second embodiment.

At step S702, the reconstruction means 14 generates the first reconstructed image and the second reconstructed image about projection data in the respective energy spectra (S702).

At step S703, the mixed ratio calculation means 15 finds for a local standard deviation of pixel values around a noticed picture element, or a local standard deviation in a local area (S703).

At step S704, the mixed ratio calculation means 15 compares a local standard deviation (SD1) in the first reconstructed image generated from the projection data acquired in the first energy spectrum with a local standard deviation (SD2) in the second reconstructed image generated from the projection data acquired in the second energy spectrum (S704). When SD1 is smaller than SD2, the first reconstructed image Img1 generated from the projection data acquired in the first energy spectrum is selected (S705). In addition, when SD1 is larger than SD2 at S704, the second reconstructed image Img2 generated from the projection data acquired in the second energy spectrum is selected (S706).

At step S707, the synthetic image generating means 16 sets as a pixel value after synthesis a pixel value in the noticed picture element or a local area in the reconstructed images selected at S705 and 706 (S707). The synthetic image generating means 16 repeats S703 to 707 every pixel or every local area.

At step S703, the synthetic image generating means 16 generates a synthetic image by mapping the pixel values after the synthesis in the respective pixels or respective local areas which are calculated at S707 (S708).

At step S709, the image display means 20 displays the synthetic image which is generated (S709).

According to this embodiment, it is possible to select an image with lower image noise between the first reconstructed image and the second reconstructed image, and to generate a synthetic image. Therefore, it is possible to generate and display the synthetic image with low image noise, and to contribute enhancement in diagnosability.

Embodiment 4

A fourth embodiment describes a form of acquiring projection data from a plurality of X-rays with different energy spectra or effective energies. In addition, although a plurality of X-rays with different effective energies are described in an example below, a case of radiography using a plurality of X-rays with different energy spectra is also the same.

Figure 8:
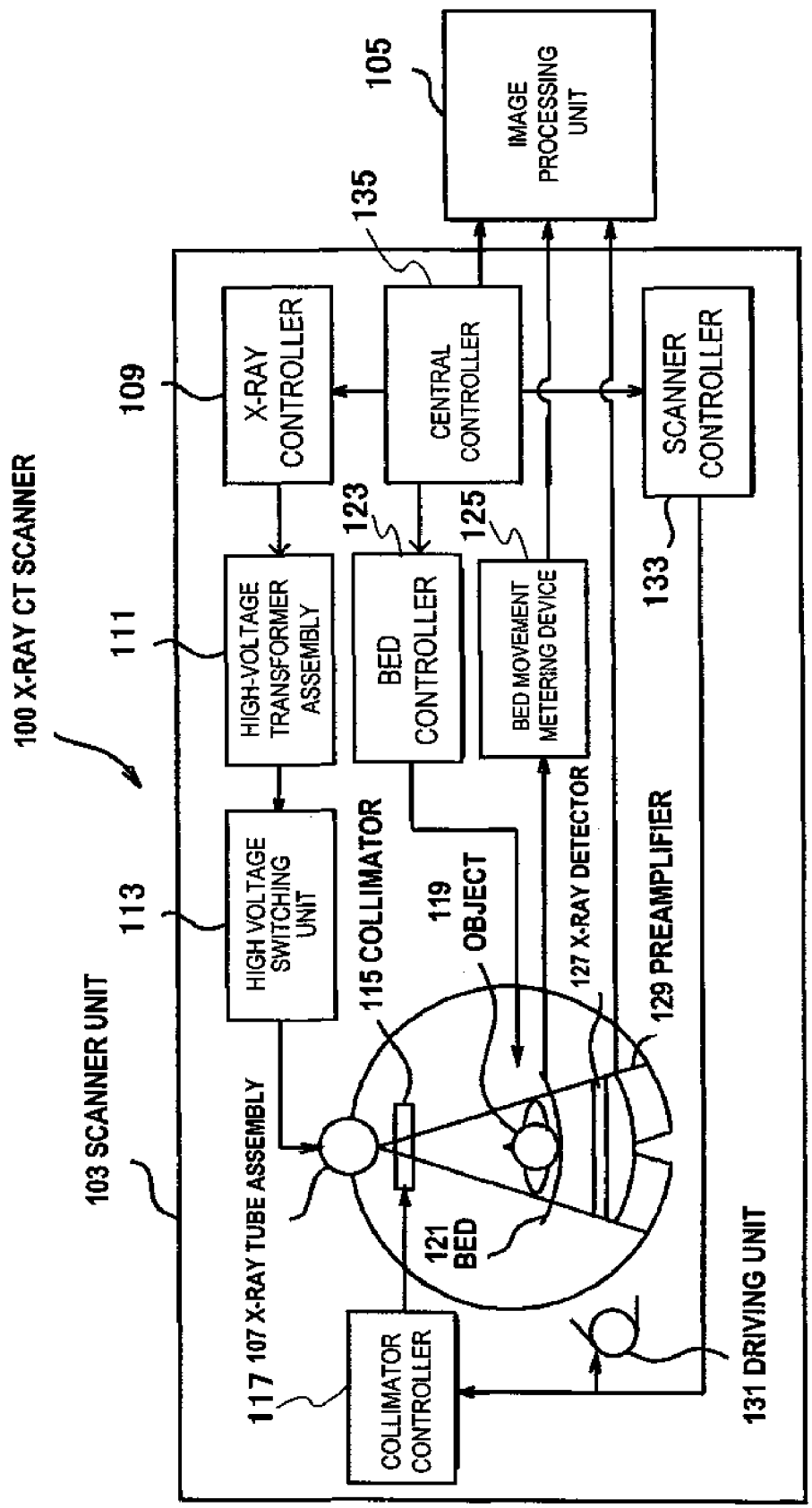
FIG. 8 is a schematic structural diagram of an X-ray CT scanner 1.

FIG. 8 is a schematic structural diagram of an X-ray CT scanner 100.

The X-ray CT scanner 100 is constructed of a scanner unit 103 and an image processing unit 105.

The X-ray CT scanner 100 is an apparatus which radiographs an object to be examined 119 and outputs a radiographed image. The X-ray CT scanner 100 radiographs the object 119 by the scanner unit 103, performs image processing in the image processing unit 105, and outputs a radiographed image.

The scanner unit 103 is equipped with an X-ray tube assembly 107, an X-ray controller 109, a high-voltage generator 111, a high-voltage switching unit 113, a collimator 115, a collimator controller 117, a bed 121, a bed controller 123, a bed movement metering device 125, an X-ray detector 127, a preamplifier 129, a driving unit 131, a scanner controller 133, a central controller 135, and the like.

The scanner unit 103 is an apparatus which radiographs the object 119, acquires projection data (radioparency data and scanning data), and transmits it to the image processing unit 105.

The X-ray tube assembly 107 is an apparatus which generates X-rays. The X-ray controller 109 is an apparatus which sends a control signal based on input information to the high-voltage generator 111. The high-voltage generator 111 is an apparatus which generates a high voltage. The high-voltage switching unit 113 is an apparatus which applies a high-voltage pulse to the X-ray tube assembly 107.

The collimator 115 is an apparatus which adjusts an irradiation area of X-rays. The collimator 115 limits irradiation directions of X-rays, and passes the X-rays necessary to project the object 119. An operation of the collimator 115 is controlled by the collimator controller 117.

The bed 121 is an apparatus which supports the object 119. The bed 121 moves the object 119 to a diagnostic measuring position of the scanner unit 103 by rise and fall movement and vertical movement. An operation of the bed 121 is controlled by the bed controller 123. The bed movement metering device 125 measures a relative movement amount of the bed 121.

The X-ray detector 127 is an apparatus which detects X-rays after transmitting the object 119. The X-ray detector has a plurality of channels which are the detecting elements of X-rays. The channels can be also constructed in many columns in a body axis direction. The preamplifier 129 is an apparatus which amplifies a signal from the X-ray detector 127, converts it into a digital signal, and sends it to the image processing unit 105.

The driving unit 131 is an apparatus which drives the X-ray tube assembly 107, X-ray detector 127, preamplifier 129, and the like in a circumferential direction to the object 119. The scanner controller 133 is an apparatus which performs motion control of the driving unit 131, and the like.

The central controller 135 is an apparatus which performs motion control of the X-ray controller 109, collimator controller 117, bed controller 123, bed movement metering device 125, scanner controller 133, and the like.

Figure 9:
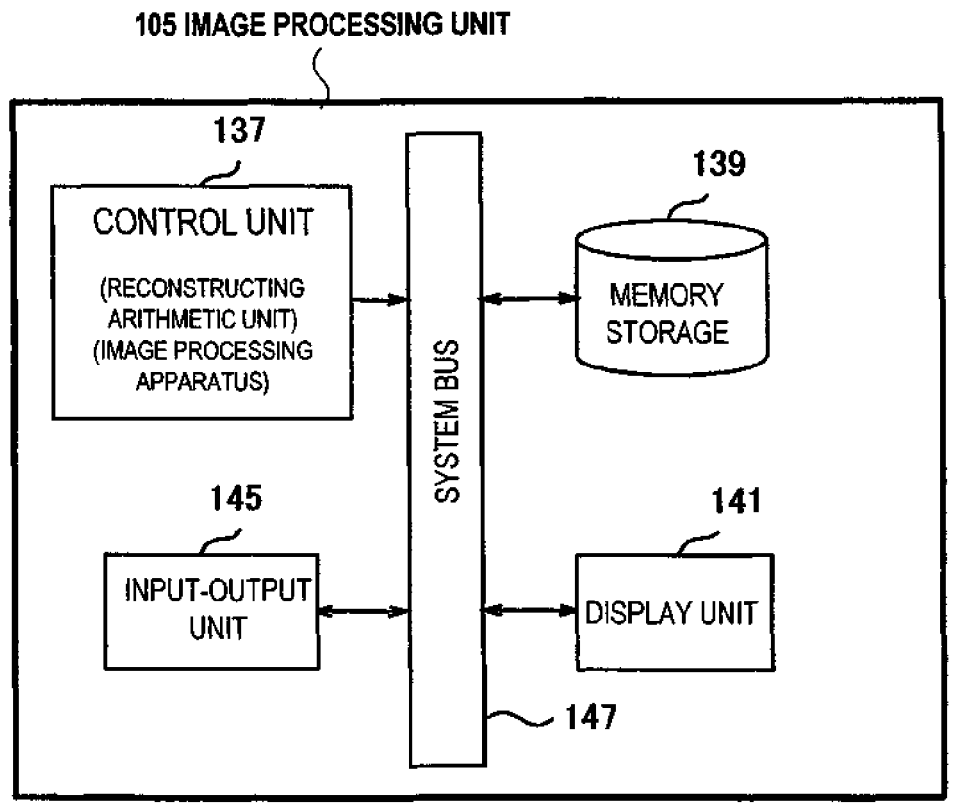
FIG. 9 is a structural diagram of an image processing unit 105 of the X-ray CT scanner 1.

FIG. 9 is a structural diagram of the image processing unit 105 of the X-ray CT scanner 100.

The image processing unit 105 is constructed of the control unit 137, memory storage 139, display unit 141, input-output unit 145, and the like being mutually connected through a system bus 147.

The image processing unit 510 is an apparatus which performs image processing with radioparency data sent from the scanner unit 103 to create image data.

The control unit 137 has a CPU (Central Processing Unit) (not illustrated), an image processor (not illustrated), a back projector (not illustrated), RAM (Random Access Memory) (not illustrated), ROM (Read Only Memory) (not illustrated), and the like.

The control unit 137 performs various data processing, and functions as a reconstructing arithmetic unit, image processing apparatus, and the like. The control unit 137 performs image reconstruction processing to projection data to create reconstructed image data, and performs image processing, such as compensation processing to projection data or reconstructed image.

The memory storage 139 is an apparatus which stores data, and has a magnetic disk, a floppy disk, memory, a magnetic tape unit, an optical disk drive, and the like. In the memory storage 139, programs which the control unit 137 executes, data necessary for program execution, an OS (Operating System), image processing data, and the like are stored.

The display unit 141 is an apparatus which displays a CT image in which the object 119 is radiographed, and is, for example, a display unit such as a CRT monitor or a liquid crystal panel.

The input-output unit 145 is an apparatus which mediates an input and an output of various data. The input-output device 145 is, for example, a console (not illustrated) equipped with a keyboard, a pointing device, and the like, and is an input-output device of various media.

The system bus 147 is a route which mediates transfer of a control signal between respective apparatuses, a data signal, and the like.

When scanning parameters (for example, bed moving speed, a tube current, a tube voltage, a slice position, and the like) and reconstruction parameters (for example, a region of interest, reconstructed image size, back projection phase width, a reconstruction filter function, and the like) are input from the input-output unit 145 of the image processing unit 105, the X-ray CT scanner 100 sends a control signal necessary for radiography to the X-ray controller 109, bed controller 123, scanner controller 133, and the like from the central controller 135 on the basis of their instructions to start radiography in response to a radiography start signal.

When starting the radiography, the X-ray CT scanner 100 send a control signal to the high-voltage generator 111 with the X-ray controller 109, applies a high voltage to the X-ray tube assembly 107, and radiates X-rays from the X-ray tube assembly 107 to the object 119. At the same time, the X-ray CT scanner 100 sends a control signal to the driving unit 131 from the scanner controller 133 to make the X-ray tube assembly 107, X-ray detector 127, preamplifier 129, and the like orbit relatively to the object 119.

On the other hand, the X-ray CT scanner 100 makes the bed 121, on which the object 119 is placed, left in a fixed location in the time of a circular orbit scan with the bed controller 123, and makes the bed 121, on which the object 119 is placed, moved in parallel in an orbital axis direction of the X-ray tube assembly 107 and the like at the time of a spiral track scan.

The radiated X-rays are limited for an irradiation area by the collimator 115, are absorbed (attenuated) in respective tissues in the object 119, pass the object 119, and are detected by the X-ray detector 127. The X-rays detected by the X-ray detector 127 are converted into a current, are amplified by the preamplifier 129, and are input into the image processing unit 105 as a projection data signal.

The control unit 137 of the image processing unit 105 performs reconstruction calculation to the input projection data signal, and performs image reconstruction processing. The control unit 137 of the image processing unit 105 stores a reconstructed image in the memory storage 139, and displays it on the display unit 141 as a CT image. In addition, after performing processing treatment of the reconstructed image, the control unit 137 of the image processing unit 105 displays it on the display unit 141.

Next, the X-ray CT scanner 1 and the like which relates to the fourth embodiment of the present invention will be described using FIGS. 10 to 13.

With referring to FIG. 10, effective energy of X-rays which the X-ray CT scanner 100 radiates will be described.

Figure 10:
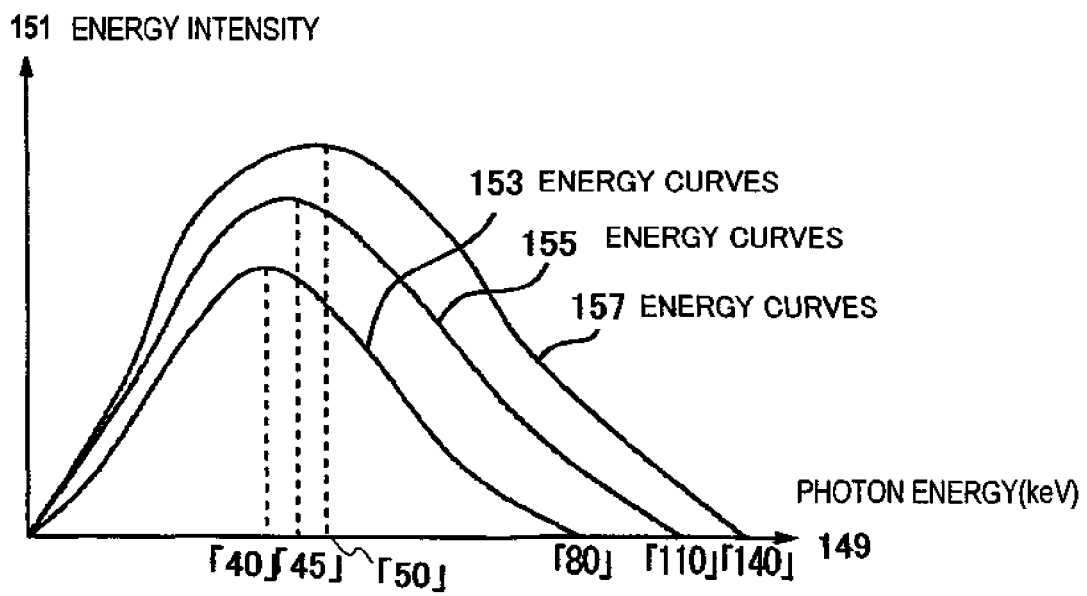
FIG. 10 is a graph illustrating energy distributions of X-rays.

FIG. 10 is a graph illustrating energy distributions of X-rays.

A horizontal axis denotes the photon energy 149 and a vertical axis denotes the energy intensity 151. In addition, the energy intensity 151 is equivalent to (photon energy)×(photon number).

An energy curve 153 denotes an energy distribution of X-rays radiated from the X-ray tube assembly 107 in the case that an X-ray tube voltage is made "80 kV".

An energy curve 155 denotes an energy distribution of X-rays radiated from the X-ray tube assembly 107 in the case that an X-ray tube voltage is made "110 kV".

An energy curve 157 denotes an energy distribution of X-rays radiated from the X-ray tube assembly 107 in the case that an X-ray tube voltage is made "140 kV".

As the energy curve 153, energy curve 155, and energy curve 157 illustrate, the photon energy and the photon number of X-ray photons which are radiated from the X-ray tube assembly 107 change with the X-ray tube voltage.

Although a largest photon energy of the X-rays illustrated in the energy curve 153 is "80 keV" corresponding to the X-ray tube voltage of 80 kV, the X-ray effective energy in consideration of an energy distribution is "40 keV", for example.

Although a largest photon energy of the X-rays illustrated in the energy curve 155 is "110 keV" corresponding to the X-ray tube voltage of 110 kV, the X-ray effective energy in consideration of an energy distribution is "45 keV", for example.

Although a largest photon energy of the X-rays illustrated in the energy curve 157 is "140 keV" corresponding to the X-ray tube voltage of 140 kV, the X-ray effective energy in consideration of an energy distribution is "50 keV", for example.

In addition, the X-ray effective energy becomes high when the X-ray tube voltage becomes high. Furthermore, as methods of changing the X-ray effective energy, besides the method of changing the X-ray tube voltage, there is a method of changing a material of a target (this will be mentioned later using FIGS. 33 to 37). Hereafter, a description will be performed as "energies are different" means "effective energies are different".

A multi-energy scan will be described with referring to FIGS. 11 to 13.

The multi-energy scan is a scanning method of acquiring a plurality of tomographic images, whose X-ray absorption coefficients are different, for the same section (slice position) by radiating a plurality of X-rays, whose effective energies are different, from the X-ray tube assembly 107.

Figure 11:
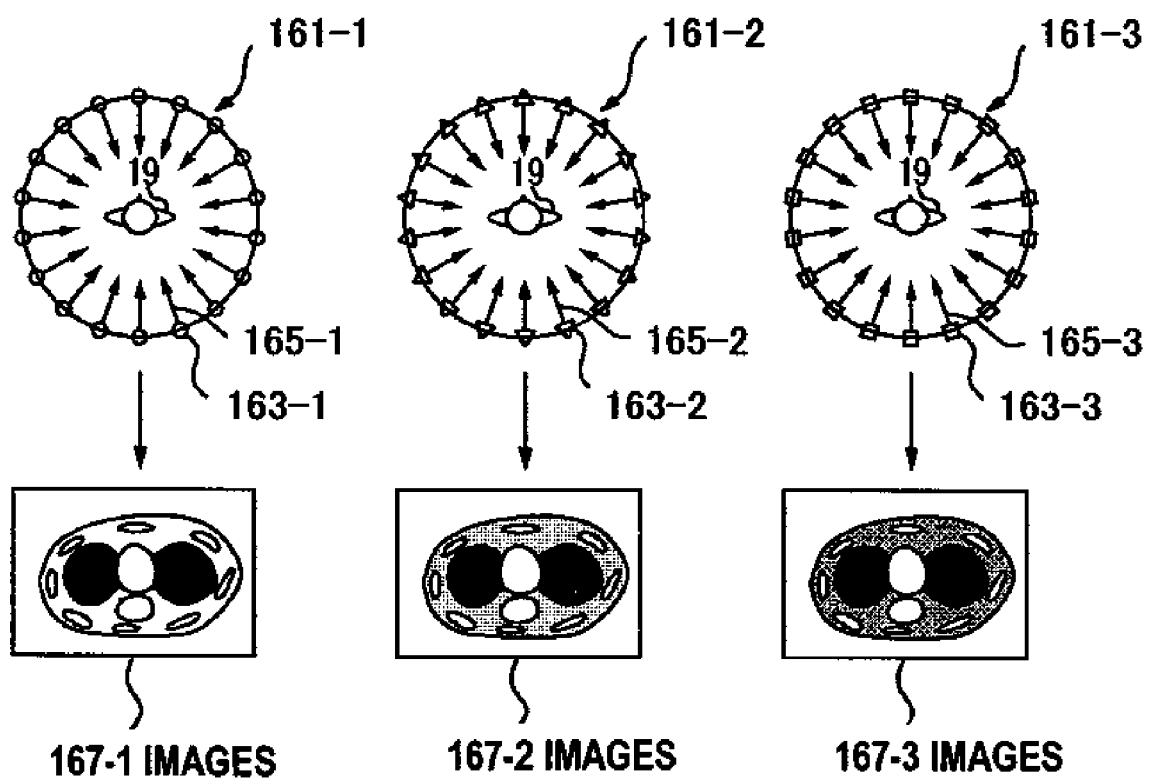
FIG. 11 includes diagrams illustrating a scanning method of scanning with changing X-ray effective energy every scan.

FIG. 11 includes diagrams illustrating a scanning method of scanning with changing the X-ray effective energy every scan.

Figures 12, 13:
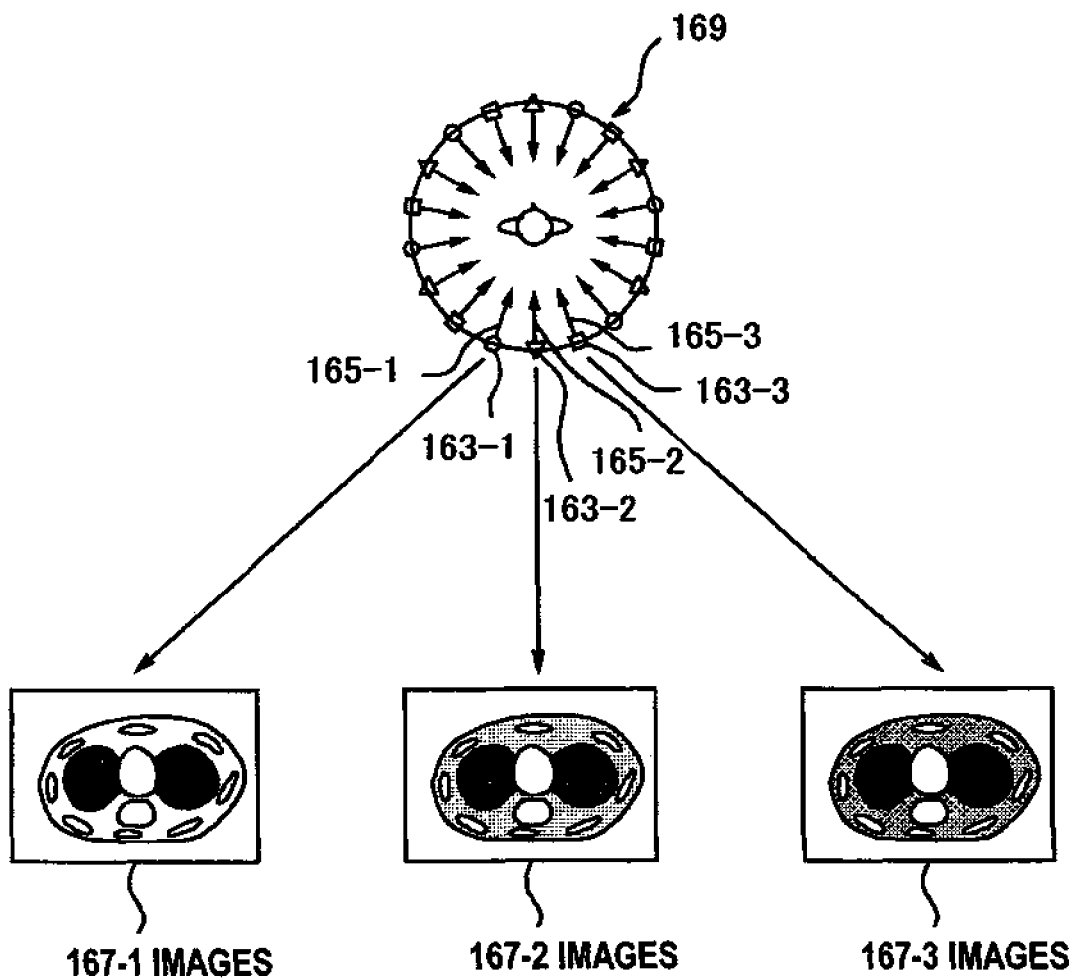
FIG. 12 includes diagrams illustrating a scanning method of scanning with changing X-ray effective energy during one scan.
FIG. 13 is a relational diagram between the irradiation position and the X-ray effective energy in FIG. 11 and FIG. 12.

FIG. 13 is a relational diagram between the irradiation position and the X-ray effective energy in FIG. 11 and FIG. 12.

In addition, one scan means radiography by performing one rotation of an environment of the object 119. That is, the X-ray CT scanner 100 acquires one tomographic image by one scan by acquiring projection data about respective projection angles (views) (0° to 360°) to give image reconstruction processing to the projection data concerned.

The X-ray CT scanner 100 radiates X-rays 165-1, 165-2, and 165-3 which have different effective energies respectively in a scan 161-1, a scan 161-2, and a scan 161-3. That is, the effective energy of the X-rays radiated in one scan (1 round: 360° rotation) is constant.

For example, the X-ray CT scanner 100 takes a radiograph with radiating the X-rays 165-1 in the first scan 161-1 at the X-ray effective energy of 30 keV from each irradiation position 163-1 ("○"), takes a radiograph with radiating the X-rays 165-2 in the second scan 163-2 at the X-ray effective energy of 50 keV from each irradiation position 163-2 ("□"), and takes a radiograph with radiating the X-rays 165-3 in the third scan 163-3 at the X-ray effective energy of 70 keV from each irradiation position 163-3 ("△").

The X-ray CT scanner 100 gives image reconstruction processing respectively to the projection data acquired in the respective scans 161-1 to 161-3, and creates images 167-1 to 167-3.

In the respective scans 16'-1 to 161-3, since X-ray effective energies are different respectively, even if being tomographic images of the same section (slice position), CT values, i.e., contrast distribution (sensitivity) of the images 167-1 to 167-3 (distributions of the X-ray absorption coefficients) are different.

FIG. 12 includes diagrams illustrating a scanning method of scanning with changing X-ray effective energy during one scan.

The X-ray CT scanner 100 radiates a plurality of X-rays whose X-ray effective energies are different according to the projection angle (view) in one scan 169. That is, the effective energy of the X-rays radiated in one scan (1 round: 360° rotation) changes.

For example, the X-ray CT scanner 100 radiates X-rays from the irradiation positions 163-1 ("○") with setting X-ray effective energy at 30 keV, radiates X-rays from the irradiation positions 163-2 ("□") with setting X-ray effective energy at 50 keV, and radiates X-rays from the irradiation positions 163-3 ("△") with setting X-ray effective energy at 70 keV.

The X-ray CT scanner 100 gives image reconstruction processing to the projection data acquired in the each irradiation position 163-1, and creates the image 167-1, gives image reconstruction processing to the projection data acquired in the each irradiation position 163-2, and creates the image 167-2, and gives image reconstruction processing to the projection data acquired in the each irradiation position 163-3, and creates the image 167-3.

In the respective irradiation positions 163-1 to 163-3, since X-ray effective energies are different respectively, even if being tomographic images of the same section (slice position), CT values, i.e., contrast distribution (sensitivity) of the images 167-1 to 167-3 (distributions of the X-ray absorption coefficients) are different.

In this way, in the fourth embodiment of the present invention, since the X-ray CT scanner 100 acquires a plurality of tomographic images (images 167-1 to 167-3), whose contrast distributions (sensitivities) are different, about the same section (slice position), it is possible to visually identify information, which cannot visually identify from one tomographic image, from other tomographic images by interpreting a plurality of tomographic images about the same section (slice position).

In addition, in FIG. 11, the X-ray CT scanner 100 takes radiographs multiple times about the same section (slice position). Hence, although a time necessary for radiography becomes long, since an amount of information increases, a noise level can be reduced.

Furthermore, in FIG. 12, the X-ray CT scanner 100 acquires a plurality of tomographic images of the same section (slice position) by one radiography (one rotation or one orbiting). Hence, since an amount of information in one tomographic image is limited, a noise level increases, but it is possible to shorten a time necessary for radiography.

In addition, although it is described in the above-mentioned embodiment to radiate a plurality of X-rays whose X-ray effective energies are different, even if a plurality of X-rays (in this case, the effective energy of each energy spectrum shall be different) whose energy spectra are different is radiated, the same operation and effect as those of the above-mentioned embodiment are obtained.

As mentioned above in detail, a multi-energy scan can be achieved easily in both sides of hardware and software according to this embodiment. In addition, it is possible to improve visibility by achieving colorization and higher contrast imaging of images obtained by the multi-energy scan radiography.

Furthermore, it becomes possible to improve speed of the operation itself of a multi-energy scan.

Furthermore, it is possible to reduce reconstruction calculation time and image processing time of image data obtained by a multi-energy scan, and to enhance quality by reducing noise.

Embodiment 5

The fifth embodiment is an embodiment of creating a synthetic color image by assigning a different monochrome color every energy spectrum or effective energy, and synthesizing these. In addition, although a case that effective energies are different is described below as an example, it is also the same as a case that energy spectra are different.

The fifth embodiment of the present invention will be described using FIGS. 14 to 17.

Color assignment to a plurality of images acquired by a multi-energy scan will be described with referring to FIGS. 14 and 15.

Figure 14:
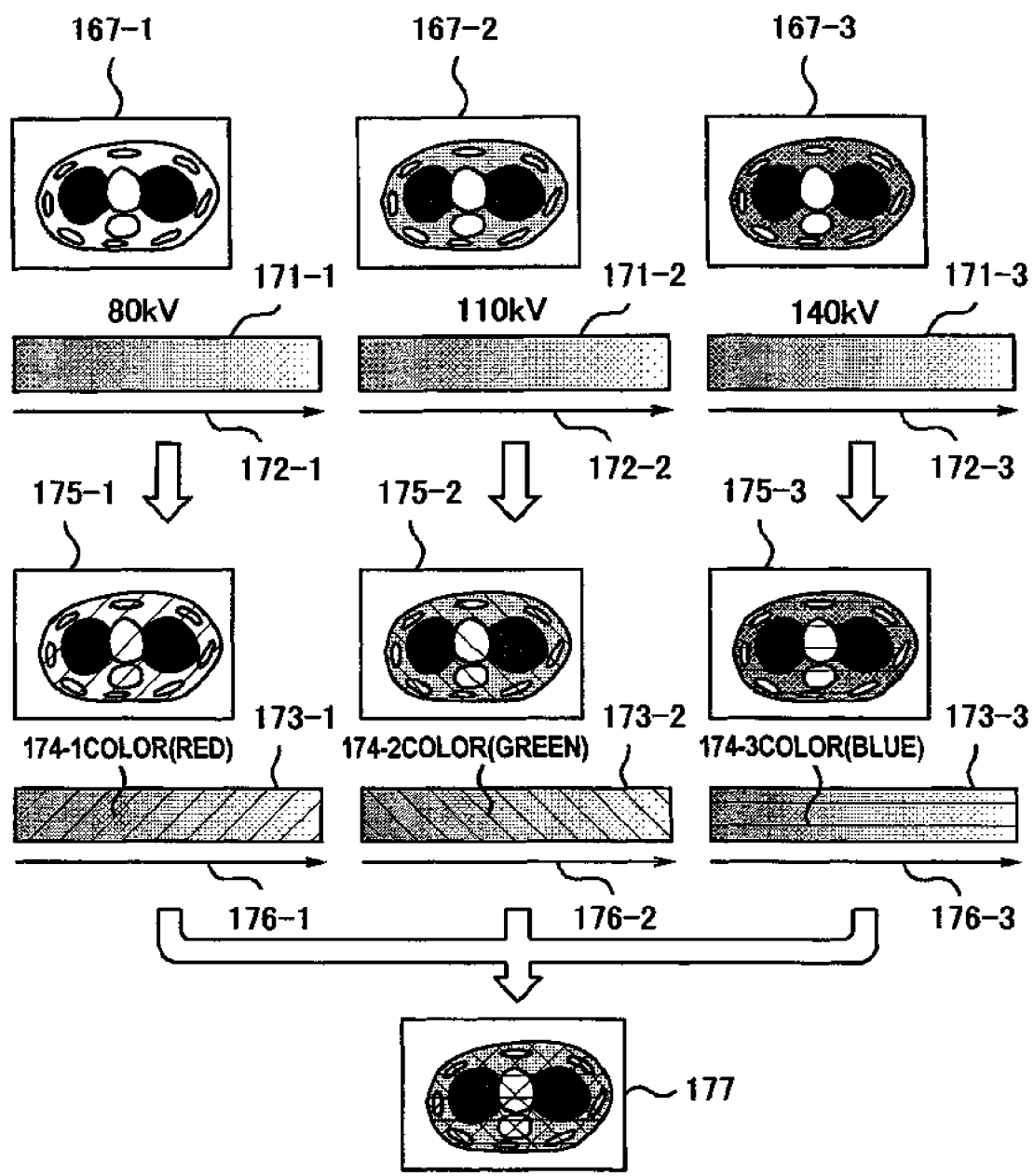
FIG. 14 is a diagram illustrating color assignment to images.

FIG. 14 is a diagram illustrating the color assignment to images.

Figure 15:
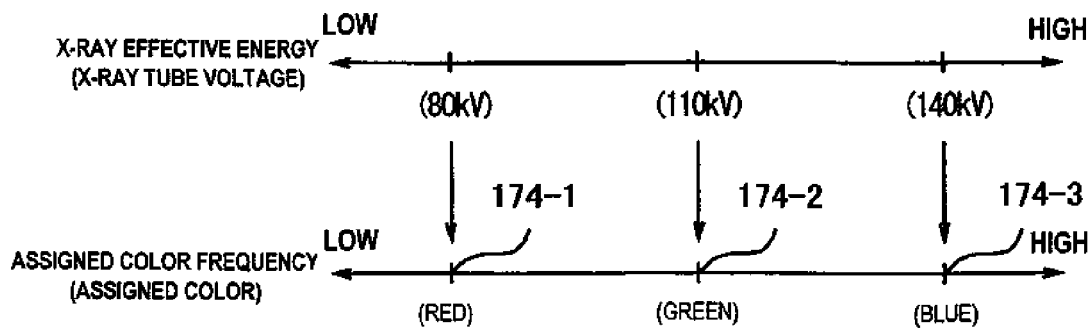
FIG. 15 is a mapping diagram between the X-ray effective energy (X-ray tube voltage) and the assigned color frequency (assigned color)

FIG. 15 is a mapping diagram between the X-ray effective energy (X-ray tube voltage) and the assigned color frequency (assigned color).

The X-ray CT scanner 100 assigns a color according to effective energy of X-rays which are radiated in order to acquire the image concerned to a plurality of images 167-1 to 167-3, whose contrast distributions (sensitivities) acquired by a multi-energy scan (refer to FIGS. 11, 12, and the like) are different to create monochrome color images 175-1 to 175-3, and synthesizes these monochrome color images to create a synthetic color image 177.

The X-ray CT scanner 100 assigns a color at a low frequency (long wave length) to an image acquired with low X-ray effective energy (low X-ray tube voltage), and assigns a color at a high frequency (short wave length) to an image acquired with high X-ray effective energy (high X-ray tube voltage). For example, the X-ray CT scanner 100 assigns a color 174-1 ("red") to an image acquired by setting the X-ray tube voltage at 80 kV, assigns a color 174-2 ("green") to an image acquired by setting the X-ray tube voltage at 110 kV, and assigns a color 174-3 ("blue") to an image acquired by setting the X-ray tube voltage at 140 kV (refer to FIG. 15).

A gradation 171-1, a gradation 171-2, and a gradation 171-3 denote gradation scales (gray scales) in images acquired by radiating X-rays with setting X-ray tube voltages at 80 kV, 110 kV, and 140 kV, respectively. In addition, they have large brightness, that is, they are displayed brightly as they go in a direction illustrated by an arrow 172.

The monochrome gradation 173-1, monochrome gradation 173-2, and monochrome gradation 173-3 denote monochrome gray scales which are created by assigning a color 174-1 ("red", "//"), a color 174-2 ("green", "\\"), and a color 174-3 ("blue" "==") to the gradation 171-1, gradation 171-2, and gradation 171-3, respectively. In addition, brightness becomes high as it goes in a direction illustrated by an arrow 176.

The X-ray CT scanner 100 assigns the color 174-1 ("red") on the basis of gradation 171-1 and the monochrome gradation 173-1 to the image 167-1 which is acquired by radiating X-rays with setting the X-ray tube voltage at 80 kV, and creates the monochrome color image 175-1. The X-ray CT scanner 100 assigns the color 174-2 ("green") on the basis of gradation 171-2 and the monochrome gradation 173-2 to the image 167-2 which is acquired by radiating X-rays with setting the X-ray tube voltage at 110 kV, and creates the monochrome color image 175-2. The X-ray CT scanner 100 assigns the color 174-3 ("green") on the basis of gradation 171-3 and the monochrome gradation 173-3 to the image 167-3 which is acquired by radiating X-rays with setting the X-ray tube voltage at 140 kV, and creates the monochrome color image 175-3.

The X-ray CT scanner 100 creates a synthetic color image 177 by synthesizing the monochrome color images 175-1 to 175-3.

In this way, the X-ray CT scanner 100 assigns colors to the image 167-1 to the image 167-3 according to the X-ray effective energy. For example, similarly to visible light, the X-ray CT scanner 100 assigns red to an image obtained with a lowest X-ray effective energy, assigns green to an image obtained with second low X-ray effective energy, and assigns blue to an image obtained with a highest X-ray effective energy, and stacks these images.

The X-ray CT scanner 100 can visualize a difference (sensitivity difference) between contrast distributions according to respective X-ray effective energies by creating the synthetic color image 177.

In addition, although the processing to the image 167 as a reconstructed image is described, the same processing can be performed not only to a reconstructed image (reconstructed image data) but also to a profile view (projection data), data acquired by these being given predetermined processing, and the like.

Hence, the image 167 not only means a reconstructed image, but also includes projection data obtained by scanning, an image obtained by the reconstructed image being given the predetermined processing, and the like.

An operation of the image processing unit 105 of the X-ray CT scanner 100 will be described with referring to FIGS. 16 and 17.

Figure 16:
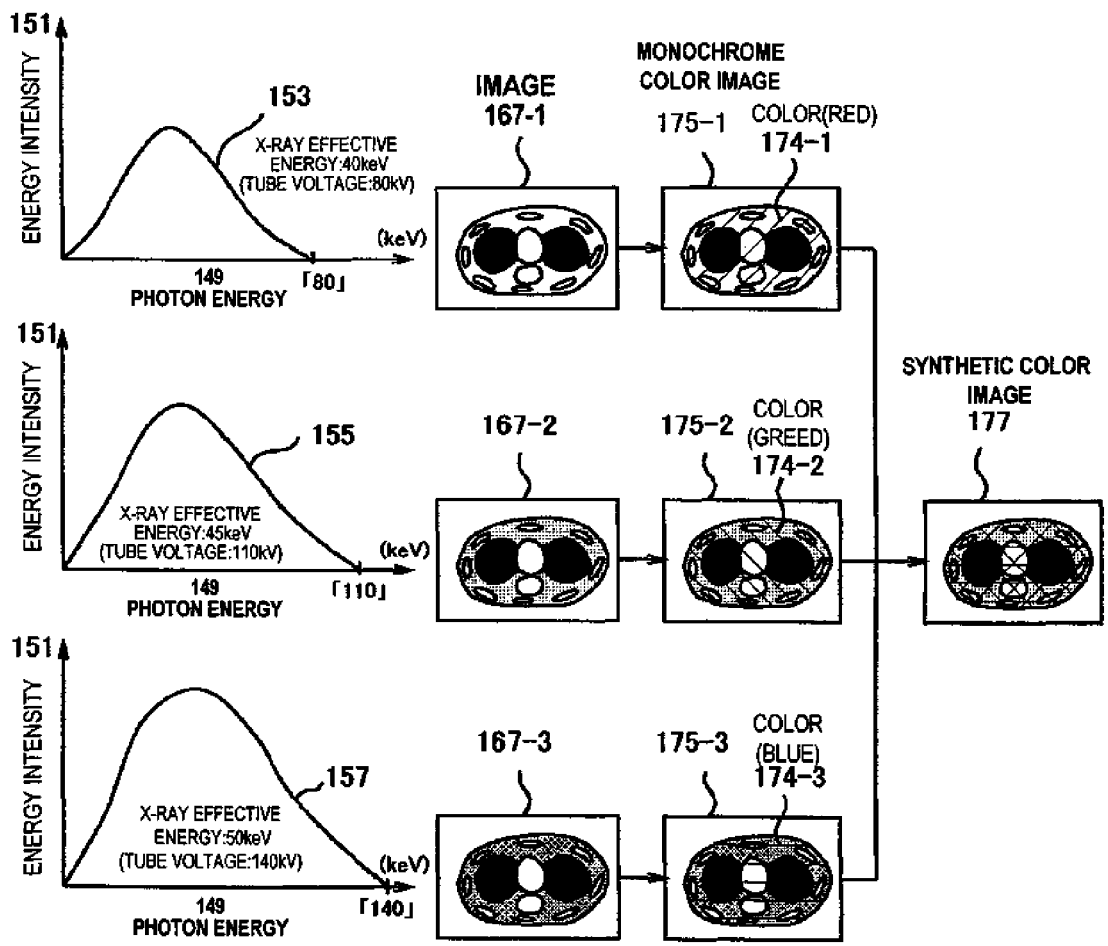
FIG. 16 includes diagrams illustrating process flows in the image processing unit 105 of the X-ray CT scanner 100 (synthetic color image creation processing)

FIG. 16 includes diagrams illustrating process flows in the image processing unit 105 of the X-ray CT scanner 100.

Figure 17:
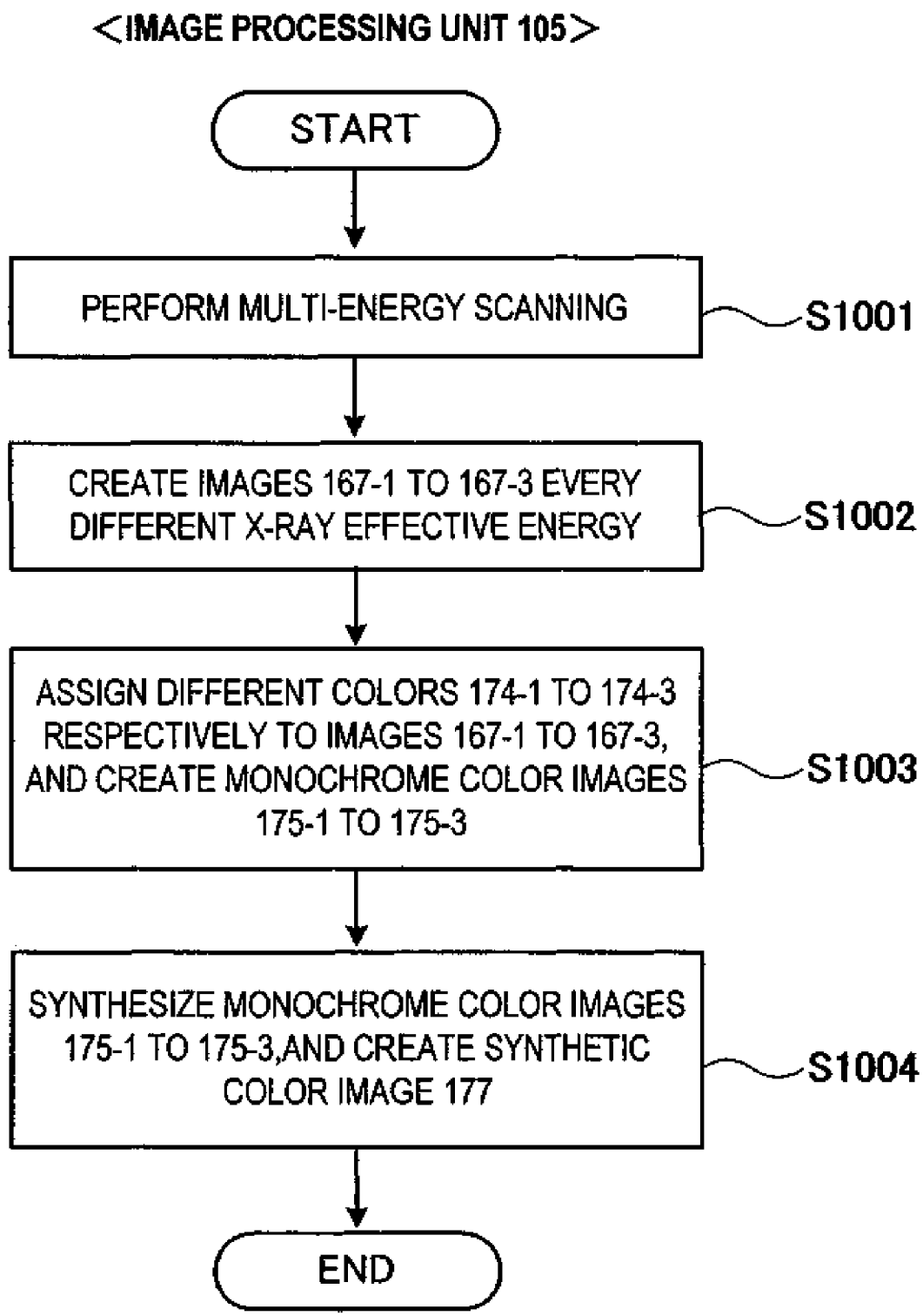
FIG. 17 is a flowchart illustrating operations of the image processing unit 105 of the X-ray CT scanner 100 (synthetic color image creation processing)

FIG. 17 is a flowchart illustrating an operation of the image processing unit 105 of the X-ray CT scanner 100.

The X-ray CT scanner 100 performs a multi-energy scan to the object 119 (step S1001). The image processing unit 105 of the X-ray CT scanner 100 acquires the image 167-1, image 167-2, and image 167-3, respectively by radiating X-rays in energy distributions illustrated by the energy curve 153, energy curve 155, and energy curve 157 (step S1002).

The image processing unit 105 assigns the color 174-1 ("red") to the image 167-1 by X-rays in lowest effective energy, and creates the monochrome color image 175-1. Similarly, the image processing unit 105 assigns the color 174-2 ("green") to the image 167-2 by X-rays in second lowest effective energy, and creates the monochrome color image 175-2. Similarly, the image processing unit 105 assigns the color 174-3 ("blue") to the image 167-3 by X-rays in highest effective energy, and obtains the monochrome color image 175-3 (step S1003).

The image processing unit 105 creates the synthetic color image 177 by synthesizing the monochrome color images 175-1 to 175-3 (step S1004).

Passing through the above process, the image processing unit 105 of the X-ray CT scanner 100 assigns colors, being different respectively, to the image 167-1 to the image 167-3 to create the monochrome color image 175-1 to the monochrome color image 175-3) and creates the synthetic color image 177 by synthesizing these monochrome color images.

In this way, since the image processing unit 105 of the X-ray CT scanner 100 creates one synthetic color image by assigning colors, being different respectively, to a plurality of images whose contrast distributions are different and synthesizes them in the fifth embodiment, it is possible to create an image with a larger amount of information, and to differentiate a diagnosis subject tissue and to enhance a difference sensitivity, tissue contrast, and visibility, and as a result, to enhance diagnostic accuracy.

In addition, although the processing to the image 167 as a reconstructed image is described, the same processing can be performed not only to a reconstructed image (reconstructed image data) but also to a profile view (projection data), data acquired by these being given predetermined processing, and the like.

Hence, the image 167, monochrome color image 75, and synthetic color image 177 not only mean reconstructed images, but also include projection data obtained by scanning. That is, a timing of performing image reconstruction processing is not limited particularly. The X-ray CT scanner 100 may perform image reconstruction processing to projection data after processing any one of step S1002 to step S1004.

According to this embodiment, by assigning colors according to the X-ray effective energy to perform display as a color image, it is possible to enhance visibility of the images obtained by the multi-energy scan.

Embodiment 6

A sixth embodiment is an embodiment of creating a differential synthetic color image. In addition, although a case that effective energies are different is described below as an example, it is also the same as a case that energy spectra are different.

Figure 18:
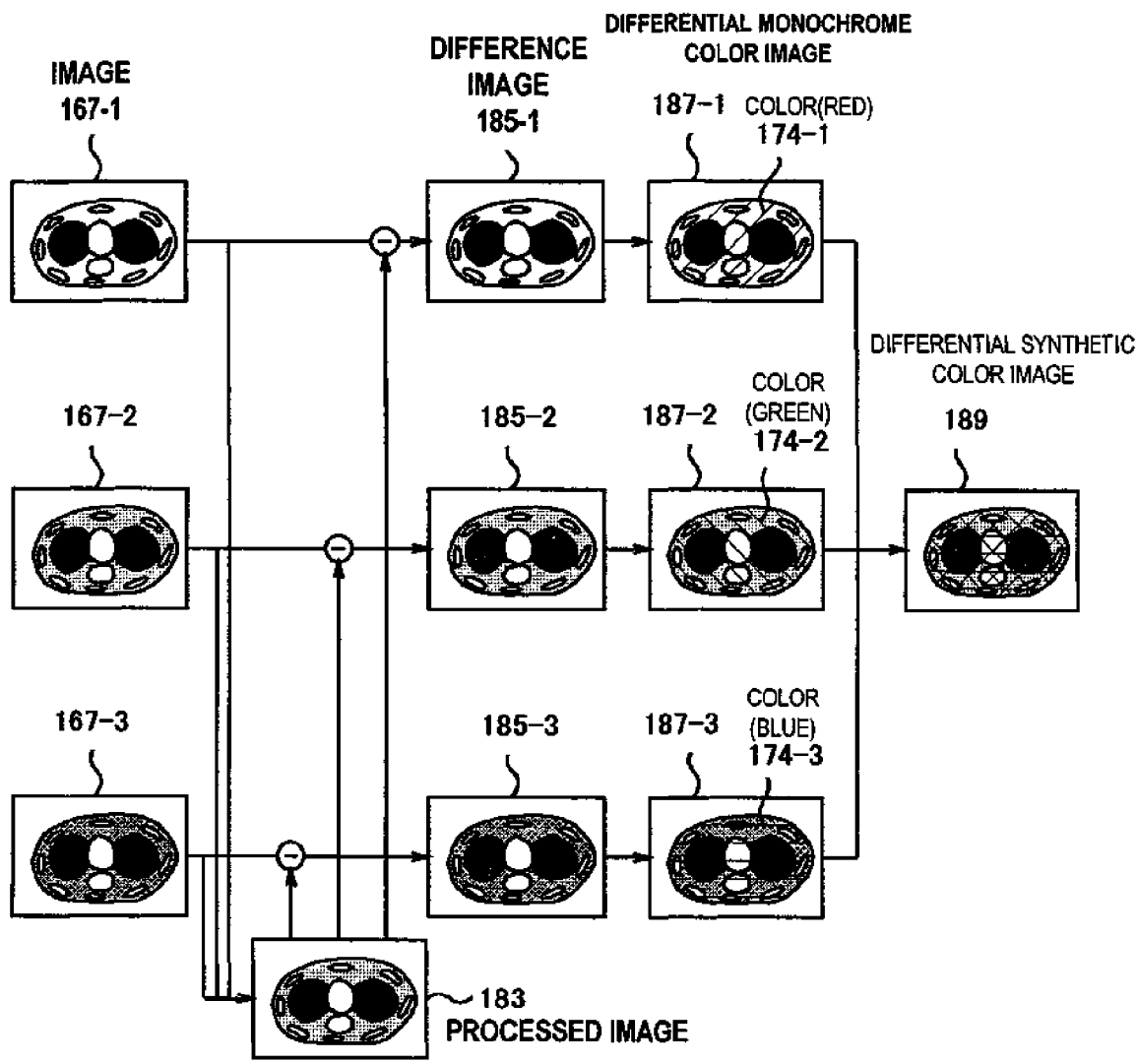
FIG. 18 includes diagrams illustrating process flows in the image processing unit 105 of the X-ray CT scanner 100 (differential synthetic color image creation processing)

The sixth embodiment of the present invention will be described using FIGS. 18 and 19. FIG. 18 includes diagrams illustrating process flows in the image processing unit 105 of the X-ray CT scanner 100.

Figure 19:
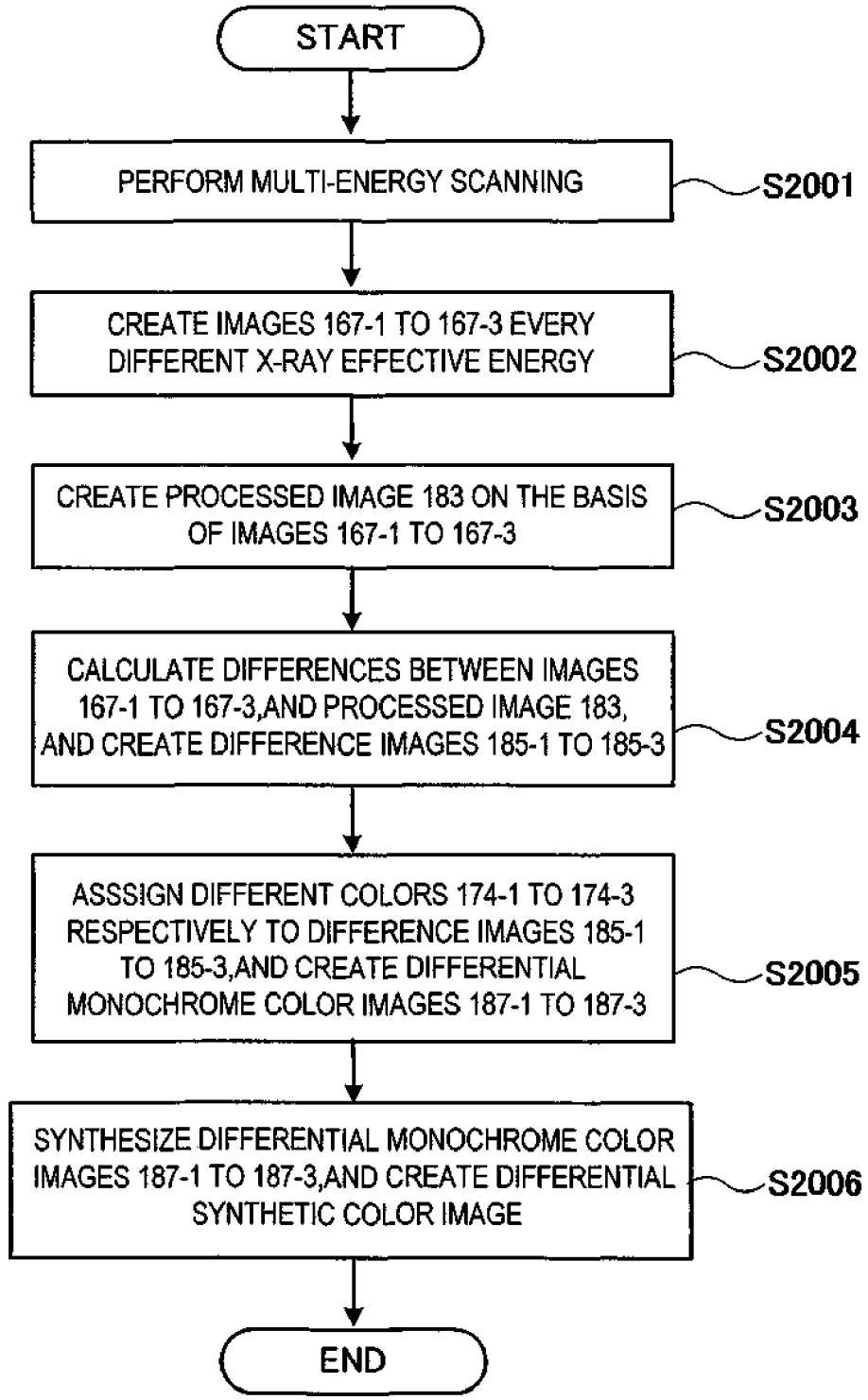
FIG. 19 is a flowchart illustrating operations of the image processing unit 105 of the X-ray CT scanner 100 (differential synthetic color image creation processing)

FIG. 19 is a flowchart illustrating an operation of the image processing unit 105 of the X-ray CT scanner 100.

The X-ray CT scanner 100 performs a multi-energy scan to the object 119 (step S2001). The image processing unit 105 of the X-ray CT scanner 100 acquires the image 167-1, image 167-2, and image 167-3, respectively by radiating X-rays in energy distributions illustrated by the energy curve 153, energy curve 155, and energy curve 157 (step S2002).

The image processing unit 105 creates a processed image 183 used as a standard for comparison for coloring on the basis of the image 167-1, image 167-2, and image 167-3 (step S2003). Furthermore, the processed image 183 is a filtered image created using, for example, a mean image, a median filter, and the like.

The image processing unit 105 calculates differences between the image 167-1, image 167-2, and image 167-3, and the processed image 183, and creates a difference image 185-1, a difference image 185-2, and a difference image 185-3 (step S2004). In addition, the image processing unit 105 may multiply by a predetermined coefficient the differential values, and may create the difference image 185-1 to the difference image 185-3.

The image processing unit 105 assigns the color 174-1 ("red") to the image 167-1 by X-rays in lowest effective energy, and creates a differential monochrome color image 187-1. Similarly, the image processing unit 105 assigns the color 174-2 ("green") to the image 167-2 by X-rays in second lowest effective energy, and creates a differential monochrome color image 187-2. Similarly, the image processing unit 105 assigns the color 174-3 ("blue") to the image 167-3 by X-rays in highest effective energy, and obtains a differential monochrome color image 187-3 (step S2005).

The image processing unit 105 creates a differential synthetic color image 189 by synthesizing the differential monochrome color images 187-1 to 187-3 (step S2006).

Passing through the above process, the image processing unit 105 of the X-ray CT scanner 100 creates the processed image 183 on the basis of the image 167-1 to the image 167-3, creates the difference image 185-1 to the difference image 185-3 to the processed image 183 concerned, assigns colors, being different respectively, creates the differential monochrome color image 187-1 to the differential monochrome color image 187-3, and creates the differential synthetic color image 189 by synthesizing these differential monochrome color images.

In this way, since the image processing unit 105 of the X-ray CT scanner 100 creates one synthetic color image by assigning colors, being different respectively, to a plurality of difference images whose contrast distributions are different and synthesizes them in the sixth embodiment, it is possible to create an image with a larger amount of information, and to differentiate a diagnosis subject tissue and to enhance a difference sensitivity, tissue contrast, and visibility, and as a result, to enhance diagnostic accuracy.

In addition, in the sixth embodiment, since the image processing unit 105 of the X-ray CT scanner 100 performs the processing to a difference image, it is possible to emphasize a difference by multiplying a difference value by a predetermined coefficient and enlarging a range. Furthermore, since the image processing unit 105 can deal with a difference value not by FLOP but by an integer arithmetic by adjusting the difference value and converting it into an integer, it is possible to decrease a load which relates to data processing.

Moreover, although the processing to the image 167 as a reconstructed image is described, the same processing can be performed not only to a reconstructed image (reconstructed image data) but also to a profile view (projection data), data acquired by these being given predetermined processing, and the like.

Hence, the image 167, processed image 183, difference image 185, differential monochrome color image 187, and differential synthetic color image 189 not only mean reconstructed images, but also include projection data obtained by scanning. That is, a timing of performing image reconstruction processing is not limited particularly. The X-ray CT scanner 100 may perform image reconstruction processing to projection data after processing any one of step S2001 to step S2006.

According to this embodiment, by assigning colors according to the X-ray effective energy to difference images between with the mean image in respective effective energies to perform display as a color image, it is possible to enhance visibility of the images obtained by the multi-energy scan.

Embodiment 7

The seventh embodiment is an embodiment of generating a processed image, obtained from a plurality of images whose X-ray effective energies are different, and an image which is constructed of pixels with a largest difference between with respective images as an emphasis image. In addition, although a case that effective energies are different is described below as an example, it is also the same as a case that energy spectra are different.

An image processing method (emphasis image creation processing) and the like which relate to the fourth embodiment of the present invention using FIGS. 20 and 21 will be described.

Figure 20:
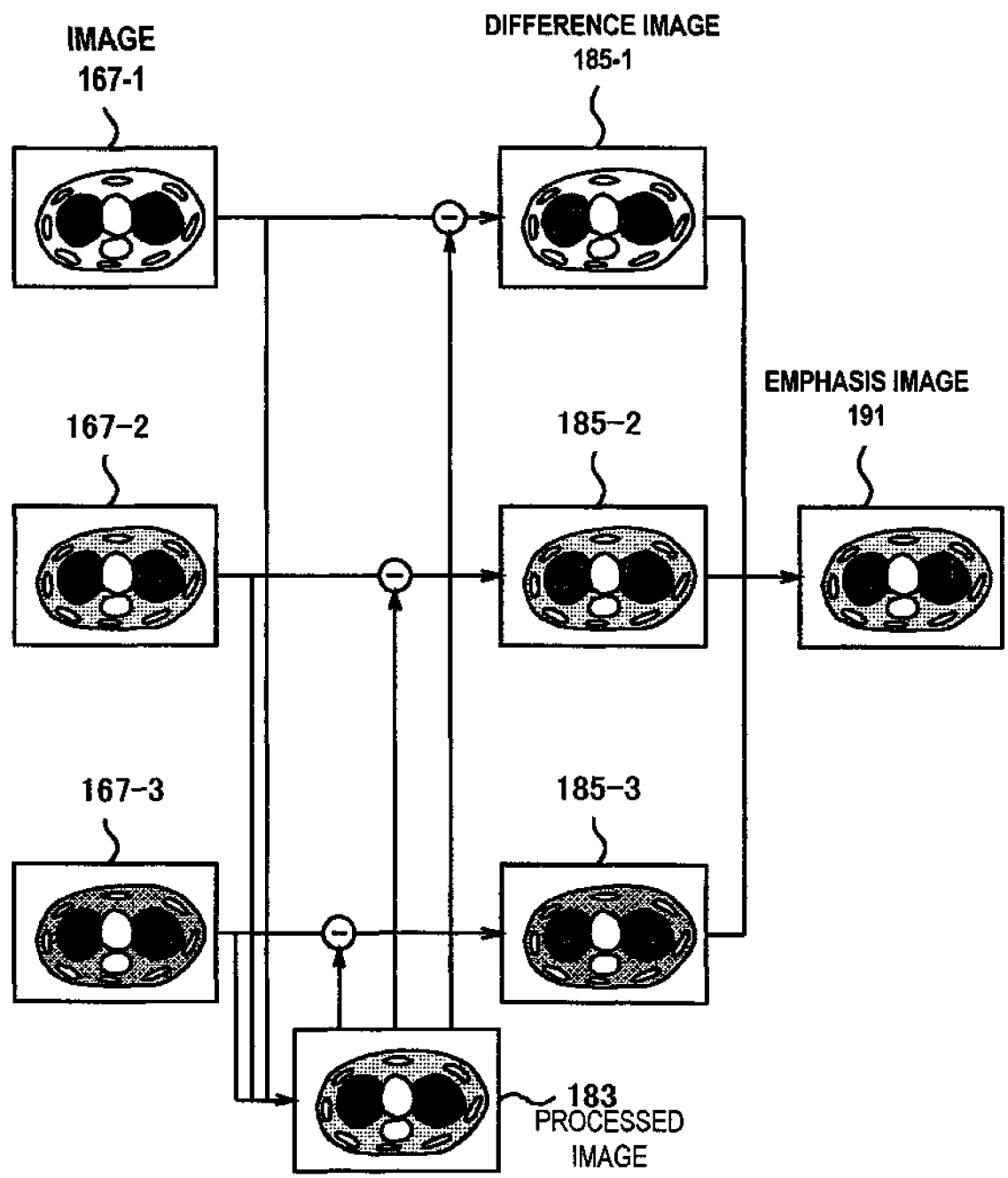
FIG. 20 includes diagrams illustrating process flows in the image processing unit 105 of the X-ray CT scanner 100 (emphasis image creation processing)

FIG. 20 includes diagrams illustrating process flows in the image processing unit 105 of the X-ray CT scanner 100.

Figure 21:
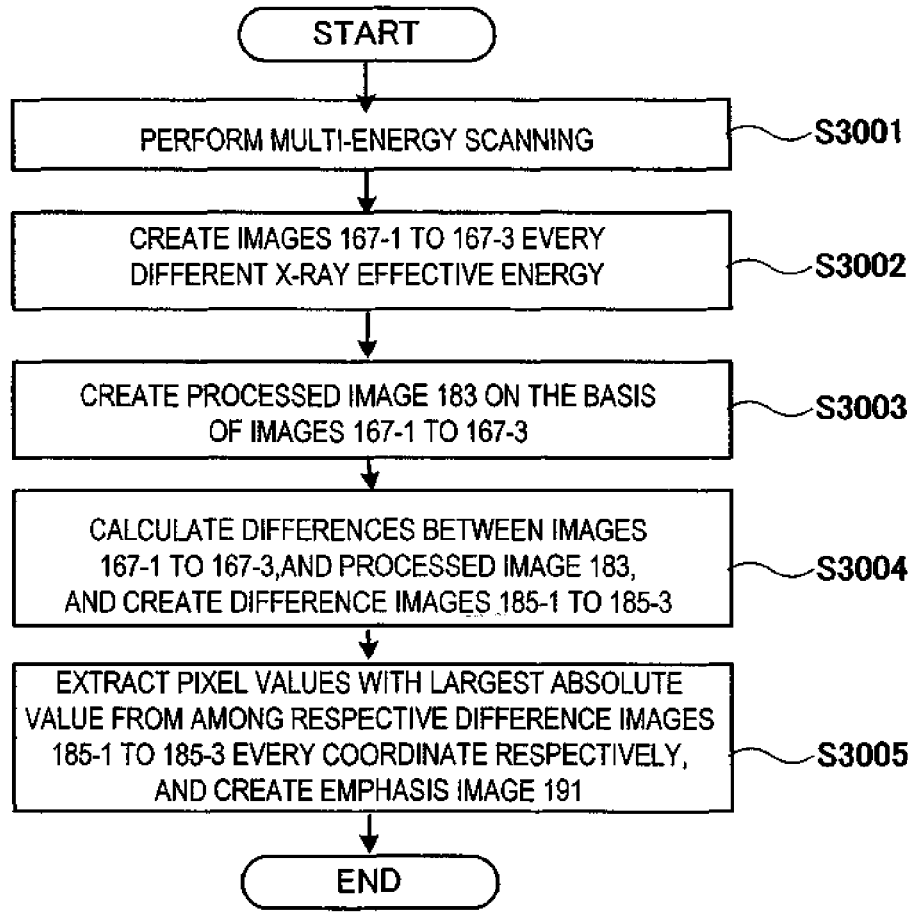
FIG. 21 is a flowchart illustrating operations of the image processing unit 105 of the X-ray CT scanner 100 (emphasis image creation processing)

FIG. 21 is a flowchart illustrating an operation of the image processing unit 105 of the X-ray CT scanner 100.

The X-ray CT scanner 100 performs a multi-energy scan to the object 119 (step S3001). The image processing unit 100 of the X-ray CT scanner 100 acquires the image 167-1, image 167-2, and image 167-3, respectively by radiating X-rays in energy distributions illustrated by the energy curve 153, energy curve 155, and energy curve 157 (step S3002).

The image processing unit 105 creates a processed image 183 used as a standard for comparison for coloring on the basis of the image 167-1, image 167-2, and image 167-3 (step S3003). In addition, the processed image 183 is a filtered image created using, for example, a mean image, a median filter, and the like.

The image processing unit 105 calculates differences between the image 167-1, image 167-2, and image 167-3, and the processed image 183, and creates a difference image 185-1, a difference image 185-2, and a difference image 185-3 (step S3004). Furthermore, the image processing unit 105 may multiply by a predetermined coefficient the differential values, and may create the difference image 185-1 to the difference image 185-3.

The image processing unit 105 extracts a pixel with a largest difference from the processed image 183 from among the respective difference images 185-1 to 185-3 every coordinates to create the emphasis image 191 (step S3005).

For example, when pixel values of the coordinates (x, y) in the difference image 185-1, difference image 185-2, and difference image 185-3 are k×Δa, k×Δb, and k×Δc respectively, a pixel value of the coordinates (x, y) in the emphasis image 191 is MAX (|k×Δa|, |k×Δb|, |k×Δc|).

In addition, Δa, Δb, and Δc denote picture element difference values between the images 167-1, 167-2, and 167-3, and the processed image 183 in coordinates (x, y) respectively, and k denotes a predetermined coefficient by which the picture element difference value concerned is multiplied. Furthermore, MAX (p, q, r) denotes a maximum of p, q, and r, and |s| denotes an absolute value of s.

Passing through the above process, the image processing unit 105 of the X-ray CT scanner 100 creates the processed image 183 on the basis of the image 167-1 to the image 167-3, creates the difference image 185-1 to the difference image 185-3 to the processed image 183 concerned, and extracts a picture element difference value, whose absolute value is largest, every coordinates to create the emphasis image 191.

In this way, in this embodiment, since the image processing unit 105 of the X-ray CT scanner 100 extracts picture element difference values, whose absolute values are largest, from a plurality of difference images whose contrast distributions are different and creates one emphasis image, it is possible to enhance contrast of the image.

In addition, although the processing to the image 167 as a reconstructed image is described, the same processing can be performed not only to a reconstructed image (reconstructed image data) but also to a profile view (projection data), data acquired by these being given predetermined processing, and the like.

Hence, the image 167, processed image 183, difference image 185, and emphasis image 191 not only mean reconstructed images, but also include projection data obtained by scanning. That is, a timing of performing image reconstruction processing is not limited particularly. The X-ray CT scanner 100 may perform image reconstruction processing to projection data after processing any one of step S3001 to step S3005.

According to this embodiment, it is possible to collect a high contrast image by generating a processed image (for example, a filtered image such as a mean image or a median filter) obtained by performing the image processing of a plurality of images whose energies are different, and which is obtained at the time of a multi-energy scan, and generating an image which is constructed of pixels that differences from the processed image in respective images are largest.

Embodiment 8

The eighth embodiment is batch arithmetic processing for making arithmetic processing, which the image processing unit 105 performs, faster, and is an embodiment of associating the radiographic position with a plurality of projection data obtained by performing a plurality of scanning in different effective energies and reconstructing them as one data. In addition, although a case that effective energies are different is described below as an example, it is also the same as a case that energy spectra are different.

The eighth embodiment of the present invention will be described using FIGS. 22 and 23. The image processing unit 105 of the X-ray CT scanner 100 performs various calculations to various data.

The data denote various data which the image processing unit 105 processes, and are, for example, projection data, reconstructed image data, calibration data, and the like. A "calculation" denotes various calculations which the image processing unit 105 performs, and is, for example, an image reconstruction calculation or the like.

Figure 22:
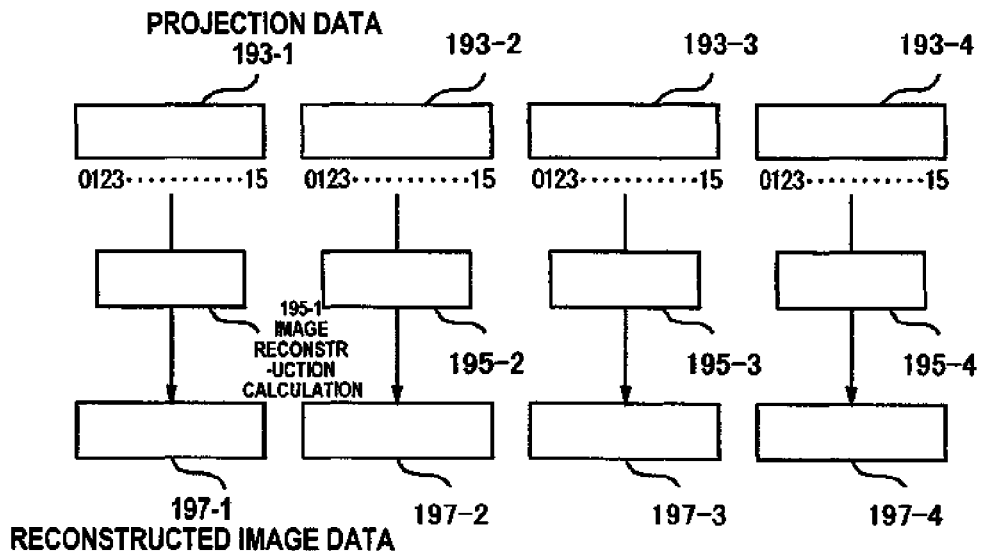
FIG. 22 is a diagram illustrating conventional data processing (individual data processing)
Figure 23:
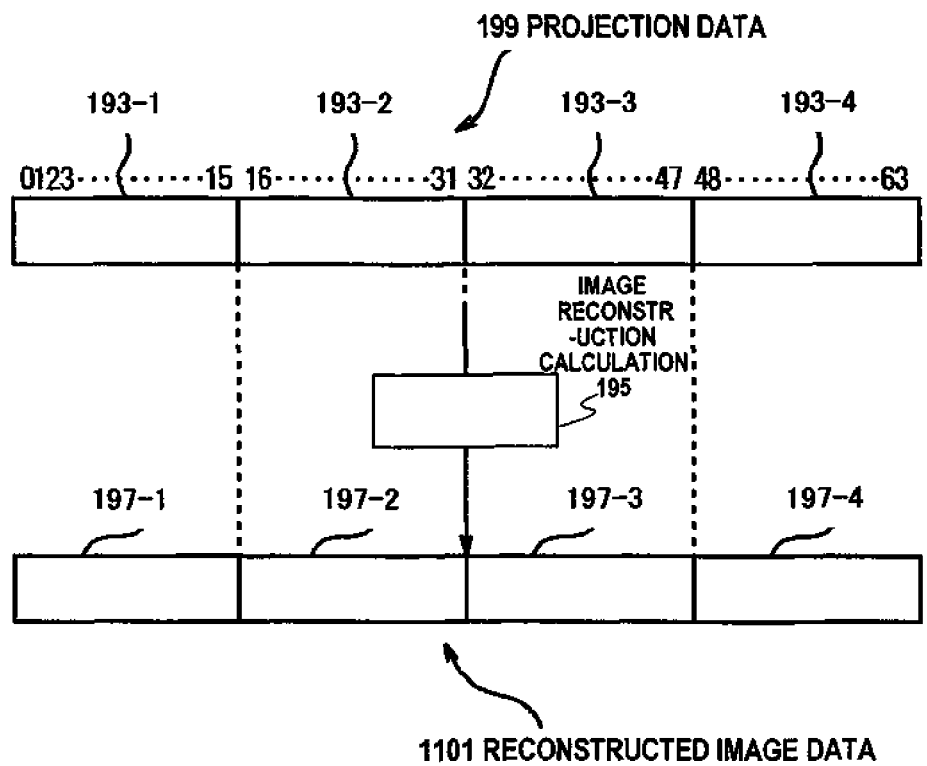
FIG. 23 is a diagram illustrating data processing (batch data processing) of the present invention.

FIGS. 22 and 23 cite and describe the image reconstruction calculation to projection data as one aspect of the "calculation" to "data".

FIG. 22 is a diagram illustrating conventional data processing (individual data processing).

The X-ray CT scanner 100 performs a multi-energy scan, and acquires projection data 193-1 to projection data 193-4 in a plurality of different X-ray effective energies.

In addition, one projection data value is assigned to each of the projection data 193-1 to the projection data 193-4.

The image processing unit 105 of the X-ray CT scanner 100 performs an image reconstruction calculation 195-1 to an image reconstruction calculation 195-4 independently respectively to the projection data 193-1 to the projection data 1934, and creates reconstructed image data 97-1 to reconstructed image data 97-4. The image processing unit 105 performs four of the image reconstruction calculation 195-1 to the image reconstruction calculation 195-4 to four of the projection data 193-1 to the projection data 193-4 which are acquired about the same tomography image.

FIG. 23 is a diagram illustrating data processing (batch data processing) of the present invention.

The X-ray CT scanner 100 performs a multi-energy scan, and acquires the projection data 193-1 to projection data 193-4 in a plurality of X-rays whose effective energies are different.

In addition, one projection data value is assigned to each of the projection data 193-1 to the projection data 193-4.

The image processing unit 105 of the X-ray CT scanner 100 combines each 16-bits of projection data 193-1 to projection data 193-4 (refer to FIG. 22) to create 64-bit projection data 199 (refer to FIG. 23).

The image processing unit 105 performs an image reconstruction calculation 195 in batch to the projection data 199 in which the projection data 193-1 to the projection data 193-4 are combined, and creates reconstructed image data 101. The image processing unit 105 acquires the respective reconstructed image data 97-1 to reconstructed image data 97-4 by dividing the reconstructed image data 101.

The image processing unit 105 performs one time of image reconstruction calculation 195 to four of the projection data 193-1 to projection data 193-4 which are acquired about the same tomography image.

Passing through in the above process, the image processing unit 105 assigns a plurality of data values to one data and performs arithmetic processing in batch to the combined data concerned, by combining a plurality of data acquired by the multi-energy scan. That is, a redundant calculation is reduced by associating the position to a plurality of projection data obtained by performing multiple times of scanning in different X-ray effective energies, and performing image processing as one data.

In this way, in the eighth embodiment of the present invention, the image processing unit 105 can reduce the number of operation times when the same arithmetic processing is performed to a plurality of data in the different X-ray effective energies, and hence, it is possible to reduce a reconstruction operation time and an image processing time.

According to this embodiment, by associating the radiographic position with a plurality of projection data obtained by performing a plurality of scanning in different X-ray effective energies and reconstructing them as one data, and specifically, by giving a plurality of data values to one data value (projection data or reconstructed image data), it is possible to reduce the reconstruction operation time and image processing time of multi-energy scan data.

Embodiment 9

The ninth embodiment of the present invention will be described using FIGS. 24 and 25. The ninth embodiment is to interpolate a plurality of projection data corresponding to different energy spectra (or effective energies), to generate projection data corresponding to energy spectra (or effective energies) different from these, and to obtain a reconstructed image. In addition, although a case that effective energies are different is described below as an example, it is also the same as a case that energy spectra are different.

Figure 24:
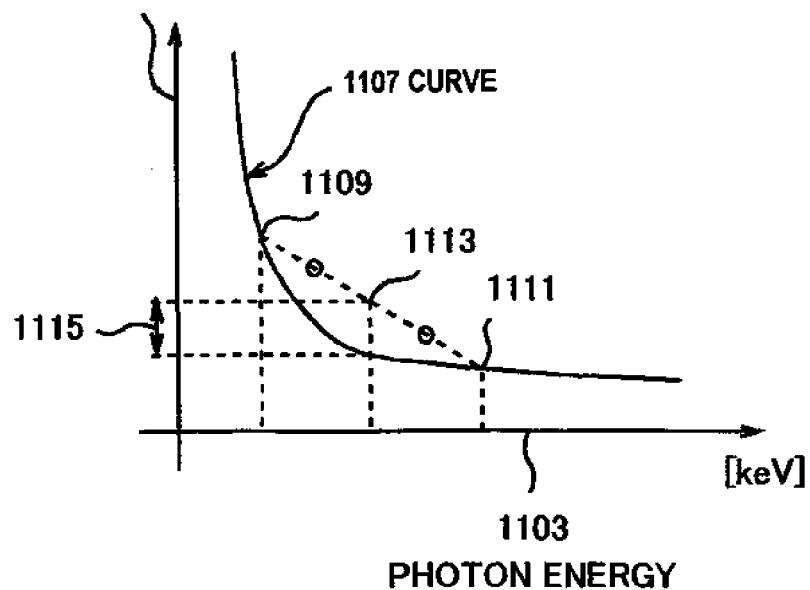
FIG. 24 is a graph illustrating relationship between the photon energy and the X-ray absorption coefficient.

FIG. 24 is a graph illustrating relationship between the photon energy and the X-ray absorption coefficient. In FIG. 24, a horizontal axis denotes the photon energy 1103 [keV], and a vertical axis denotes the X-ray absorption coefficient 1105 [cm²/g].

The X-ray absorption coefficient which is unique to each substance has high nonlinearity according to the transmitting X-ray effective energy. The X-ray absorption coefficient is expressed in a nonlinear function of photon energy. Hence, when data is newly created by performing two-point interpolation (linear interpolation) between two data on the basis of this function, a large error arises.

In actual measurement, when the X-ray CT scanner 100 acquires data, which a point 1109 expresses, and data which a point 1111 expresses, the image processing unit 105 of the X-ray CT scanner 100 performs linear interpolation on the basis of the point 1109 and point 1111 to create newly data which a point 1113 expresses.

An error 1115 in the X-ray absorption coefficient 1105 also becomes large proportionately in a part with large nonlinearity in a curve 1107.

Figure 25:
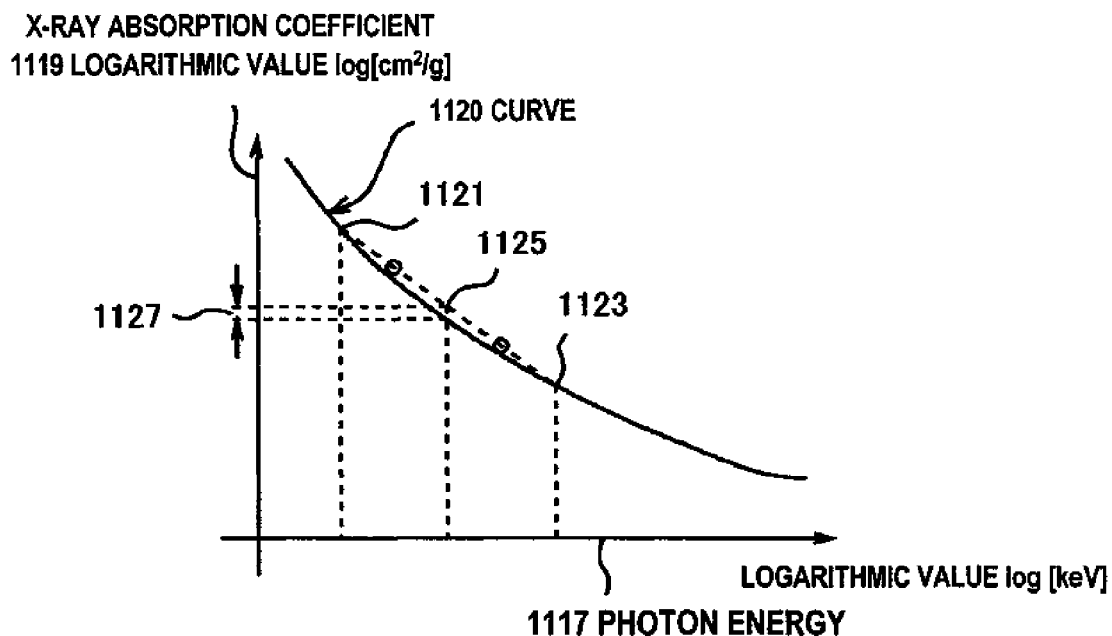
FIG. 25 is a graph illustrating relationship between the photon energy and the X-ray absorption coefficient (logarithmic space)

FIG. 25 is a graph illustrating relationship between the photon energy and the X-ray absorption coefficient.

In FIG. 25, a horizontal axis expresses the logarithmic value 1117 (log [keV]) of the photon energy 1103 [keV], and a vertical axis expresses the logarithmic value 1119 (log [cm²/g]) of the X-ray absorption coefficient 1105 [cm²/g].

A graph illustrated in FIG. 25 is obtained by giving logarithmic transformation to both the axes of the graph illustrated in FIG. 24. A curve 1107 in FIG. 24 is converted into a curve 1121 in FIG. 25. In the curve 1121, in comparison with the curve 1107, nonlinearity is distinctly decreases, and linearity improves.

In actual measurement, when the X-ray CT scanner 100 acquires data, which the point 1109 expresses in FIG. 24, and data which the point 1111 expresses, the image processing unit 105 of the X-ray CT scanner 100 gives logarithmic transformation to them respectively to convert them into data which a point 1121 and a point 1123 in FIG. 25 illustrate.

In addition, the image processing unit 105 performs logarithmic transformation of the photon energy 1103 and the X-ray absorption coefficient 1105 to convert them into the logarithmic value 1117 of the photon energy and the logarithmic value 1119 of the X-ray absorption coefficient.

The image processing unit 105 performs linear interpolation on the basis of the point 1121 and point 1123 to create newly data which a point 1125 expresses.

In the curve 1121 in FIG. 25, since linearity is improved in comparison with the curve 1107 in FIG. 24, an error 1127 in the logarithmic value 1119 of the X-ray absorption coefficient also becomes small proportionately. Therefore, the X-ray CT scanner 100 can obtain a value very near an actual X-ray absorption coefficient.

In this way, in the ninth embodiment, the image processing unit 105 of the X-ray CT scanner 100 can calculate data of the X-ray absorption coefficient in the X-ray effective energy, and the like, which are not measured, with high precision by performing interpolation in a two-axes logarithmic space.

In addition, the image processing unit 105 of the X-ray CT scanner 100 can create data in a multi-energy scan using limited data of the X-ray absorption coefficient and the like to be able to reduce exposure, exposure time, and data volume to be held.

According to this embodiment, it is possible to generate data of different X-ray energies with high precision by estimating an attenuated coefficient value (projection data value) of desired energy by interpolating in a logarithmic space a plurality of projection data obtained by performing multiple times of scanning in different X-ray energies in the X-ray CT scanner, and hence, it is possible to reduce an amount of exposures in the case of acquiring radiographic images of three or more kinds of energies in a multi-energy scan, to reduce a necessary calibration data count, and to shorten exposure time of calibration data.

Embodiment 10

The tenth embodiment is an embodiment of performing image processing for smoothing noise. In addition, although a case that effective energies are different is described below as an example, it is also the same as a case that energy spectra are different.

The tenth embodiment of the present invention will be described using FIG. 26.

Figure 26:
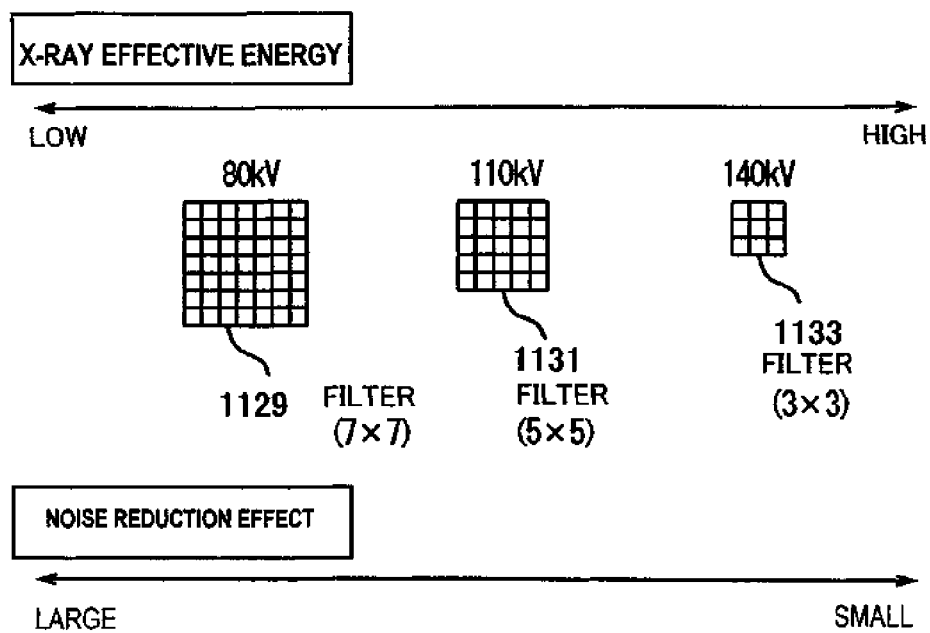
FIG. 26 is a diagram illustrating a setup method of a filtering parameter.

FIG. 26 is a diagram illustrating a setup method of a filtering parameter.

When performing filtering to projection data or reconstructed image data which is acquired in a multi-energy scan, the image processing unit 105 of the X-ray CT scanner 100 changes kernel size of a filter according to largeness of X-ray effective energy.

For example, the image processing unit 105 gives smoothing filtering to projection data, acquired at the X-ray tube voltage of 80 kV, with a filter 1129 which has 7×7 filter kernel size in a channel direction and a view direction, gives smoothing filtering to projection data, acquired at the X-ray tube voltage of 110 kV, with a filter 1131 which has 5×5 filter kernel size in the channel direction and view direction, and gives smoothing filtering to projection data, acquired at the X-ray tube voltage of 140 kV, with a filter 1133 which has 3×3 filter kernel size in the channel direction and view direction. The image processing unit 105 performs averaging processing of 9 adjacent pixels including an object picture element in smoothing.

As X-ray effective energy becomes large, an amount of information to be acquired increases, and noise in acquired data decreases. In addition, a smoothing effect and a noise reduction effect increase as kernel size of a filter becomes large.

Then, the image processing unit 105 changes the kernel size of a filter according to X-ray effective energy, and performs image processing. The image processing unit 105 lessens the kernel size of a filter to projection data or a reconstructed image acquired by high X-ray effective energy and performs filtering, and enlarges the kernel size of a filter to projection data or a reconstructed image acquired by low X-ray effective energy and performs filtering.

Hence, a difference between numerical values of an SN ratio (Signal to Noise Ratio) and a CN ratio (Contrast to Noise Ratio) in respective images (projection data or reconstructed image) becomes small.

In addition, it is desirable to equalize the SN ratio or CN ratio in respective images (projection data or reconstructed image) as much as possible by changing the kernel size of a filter according to X-ray effective energy.

Nevertheless, only by control of the kernel size of a filter, the SN ratio or CN ratio does not always become an equal value. Hence, it is desirable to combine and apply various image processing filters.

Regarding the image processing filter, without limiting to a smoothing filter, a median filter, a weighting addition filter, a similarity filter, an adaptive filter obtained by combining these, or the like may be used. In addition, although the two-dimensional filter in the channel direction and view direction of projection data is described, a two-dimensional filter in any directions including a column direction may be sufficient, and a three-dimensional filter in a channel direction, a view direction, and a column direction can be also used.

Furthermore, a target of the processing by the above-described image processing filter may not be limited to projection data, but may be a reconstructed image. In this case, filtering can be performed at arbitrary dimensions including an x direction, a y direction, and a z direction.

In this way, in the seventh embodiment, since the image processing unit 105 of the X-ray CT scanner 100 applies a filter with a large noise reduction effect to an image (projection data or reconstructed image) acquired with X-rays of low effective energy, and applies a filter with a small noise reduction effect to an image (projection data or reconstructed image) acquired with X-rays of high effective energy, it is possible to lessen the difference between numerical values of the SN ratio and CN ratio in respective images (projection data or reconstructed image) acquired by the multi-energy scan.

In addition, in the tenth embodiment, since the SN ratio and CN ratio are equalized by software processing in the image processing unit 105, it is not necessary to change device construction and motion control in a side of the scanner unit 103.

Embodiment 11

An eleventh embodiment is an embodiment of changing scanning speed according to effective energy of X-rays. Furthermore, although a case that effective energies are different is described below as an example, it is also the same as a case that energy spectra are different.

An X-ray CT scanner 100 which relates to the eleventh embodiment of the present invention will be described using FIGS. 27 to 28.

FIG. 27 is a diagram illustrating control of scanning speed according to the X-ray effective energy.

FIG. 28 is a relational diagram among the irradiation position, the X-ray effective energy, and the scanning speed in FIG. 27.

When radiating X-rays from the X-ray tube assembly 107 to the object 119, the scanner unit 103 of the X-ray CT scanner 100 changes speed 1135 of the scan 161 according to X-ray effective energy. That is, the scanner unit 103 changes time, needed for X-ray tube assembly 107, X-ray detector 127, and the like perform one rotation around the object 119, according to the effective energy of X-rays which are radiated from the X-ray tube assembly 107.

For example, the scanner unit 103 radiates X-rays 165-1 with setting scanning speed 1135-1 at 1.0 second/rotation when taking a radiograph at an X-ray tube voltage of 80 kV (scan 161-1) (1.0-second scan), radiates X-rays 165-2 with setting scanning speed 1135-2 at 0.5 second/rotation when taking a radiograph at an X-ray tube voltage of 110 kV (scan 161-2) (0.5-second scan), and radiates X-rays 165-3 with setting scanning speed 1135-3 at 0.33 second/rotation when taking a radiograph at an X-ray tube voltage of 140 kV (scan 161-3) (0.33-second scan).

When other conditions in the scan 161-1 to the scan 161-3 are the same, an amount of information obtained by one rotation increases and noise in acquired data decrease, as the scanning speed 1135 becomes small.

Then, the scanner unit 103 changes the scanning speed according to the X-ray effective energy to perform X-ray irradiation from the X-ray tube assembly 107. The X-ray CT scanner 100 takes a radiograph with lessening the scanning speed in the case of radiating X-rays at low effective energy, and takes a radiograph with enlarging the scanning speed in the case of radiating X-rays at high effective energy.

Hence, a difference between numerical values of the SN ratio and CN ratio in respective images (projection data or reconstructed image) becomes small.

In addition, it is desirable to equalize the SN ratio or CN ratio in respective images (projection data or reconstructed image) as much as possible by changing the scanning speed according to the X-ray effective energy.

In this way, in the eleventh embodiment, since the scanner unit 103 of the X-ray CT scanner 100 takes a radiograph with lessening the scanning speed in the case of radiating X-rays at low effective energy, and takes a radiograph with enlarging the scanning speed in the case of radiating X-rays at high effective energy, it is possible to lessen the difference between numerical values of the SN ratio and CN ratio in respective images (projection data or reconstructed image) acquired by the multi-energy scan.

In addition, since the SN ratio and CN ratio are equalized by motion control in the side of the scanner unit 103 in the eighth embodiment, it is not necessary to change the software in the image processing unit 105.

Embodiment 12

A twelfth embodiment is an embodiment of changing a tube current according to X-ray effective energy. Furthermore, although a case that effective energies are different is described below as an example, it is also the same as a case that energy spectra are different.

An X-ray CT scanner 100 which relates to the twelfth embodiment of the present invention will be described using FIGS. 29 to 30.

FIG. 29 is a diagram illustrating control of the X-ray tube current according to the X-ray effective energy.

Figures 30, 31, 32:
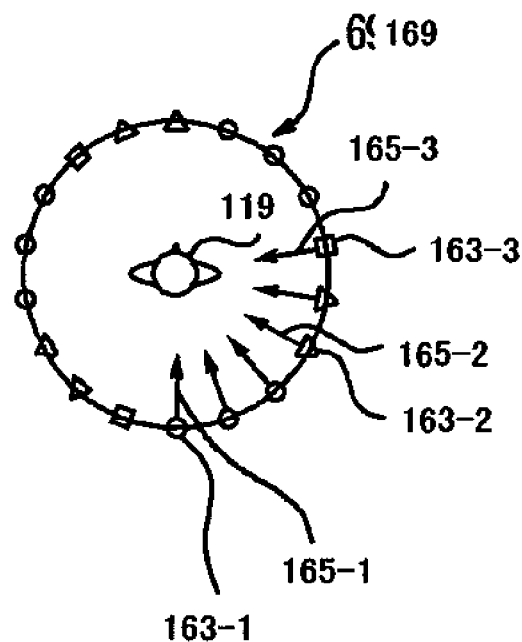
FIG. 30 is a relational diagram among the irradiation position, the X-ray effective energy, and the X-ray tube current in FIG. 29.
FIG. 31 is a diagram illustrating control of the ratio of view count according to the X-ray effective energy.
FIG. 32 is a relational diagram among the irradiation position, the X-ray effective energy, and the view count in FIG. 31.

FIG. 30 is a relational diagram among the irradiation position, the X-ray effective energy, and the X-ray tube current in FIG. 29.

When radiating X-rays from the X-ray tube assembly 107 to the object 119, the scanner unit 103 of the X-ray CT scanner 100 changes an X-ray tube current in the X-ray tube assembly 107 according to the X-ray effective energy.

The scanner unit 103 radiates X-rays 165 at effective energies different every position 163 of the scan 169 in the scan 169 in the case that the X-ray tube assembly 107, X-ray detector 127, and the like perform one rotation around the object 119.

For example, the scanner unit 103 takes a radiograph with setting an X-ray tube current at 300 mA and radiating the X-rays 165-1 in the position 163-1 where the X-ray tube voltage becomes 80 kV, takes a radiograph with setting an X-ray tube current at 159 mA and radiating the X-rays 165-2 in the position 163-2 where the X-ray tube voltage becomes 110 kV, and takes a radiograph with setting an X-ray tube current at 99 mA and radiating the X-rays 165-3 in the position 163-3 where the X-ray tube voltage becomes 140 kV.

When other conditions in the scan 169 are the same, an amount of information obtained by one rotation increases and noise in acquired data decrease, as the X-ray tube current becomes large.

Then, the scanner unit 103 changes the X-ray tube current according to the X-ray effective energy to perform X-ray irradiation from the X-ray tube assembly 107. The scanner unit 103 takes a radiograph with enlarging the X-ray tube current in the case of radiating X-rays at low effective energy, and takes a radiograph with lessening the X-ray tube current in the case of radiating X-rays at high effective energy.

Hence, a difference between numerical values of the SN ratio and CN ratio in respective images (projection data or reconstructed image) becomes small.

In addition, it is desirable to equalize the SN ratio or CN ratio in respective images (projection data or reconstructed image) as much as possible by changing the X-ray tube current according to the X-ray effective energy.

In addition, when changing X-ray effective energy in one rotation, it is desirable to change the X-ray tube current in real time according to the X-ray effective energy concerned.

In this way, in the twelfth embodiment, the scanner unit 103 of the X-ray CT scanner 100 takes a radiograph with enlarging the X-ray tube current in the case of radiating X-rays at low effective energy and takes a radiograph with lessening the X-ray tube current in the case of radiating X-rays at high effective energy, it is possible to lessen the difference between numerical values of the SN ratio and CN ratio in respective images (projection data or reconstructed image) acquired by the multi-energy scan.

Furthermore, since the SN ratio and CN ratio are equalized by motion control in the side of the scanner unit 103 in the twelfth embodiment, it is not necessary to change the software in the image processing unit 105.

Moreover, in the eleventh embodiment, it is necessary to change scanning speed during one scan in the case of a multi-energy scan in one scan, and hence, control is hard. On the other hand, in the twelfth embodiment, the X-ray tube current can be changed at high speed, and hence, it is possible to respond to the multi-energy scan in one scan easily.

Embodiment 13

The thirteenth embodiment is an embodiment of changing the number of radiography positions (this is equivalent to a radiation range ratio) according to X-ray effective energy. In addition, although a case that effective energies are different is described below as an example, it is also the same as a case that energy spectra are different.

An X-ray CT scanner 100 which relates to the thirteenth embodiment of the present invention will be described using FIGS. 31 to 32.

FIG. 31 is a diagram illustrating control of the ratio of view count according to the X-ray effective energy.

FIG. 32 is a relational diagram among the irradiation position, the X-ray effective energy, and the view count in FIG. 31.

When radiating X-rays from the X-ray tube assembly 107 to the object 119, the scanner unit 103 of the X-ray CT scanner 100 changes a ratio of scanning position count (view count) according to the X-ray effective energy.

The scanner unit 103 changes a ratio of the number of positions 163, in which X-rays 165 are radiated, every X-ray effective energy in the scan 169 in the case that the X-ray tube assembly 107, X-ray detector 127, and the like perform one rotation around the object 119.

For example, the scanner unit 103 makes the ratio of the positions 163-1, radiographed at the X-ray tube voltage of 80 kV, 54% during one rotation, makes the ratio of the positions 163-2, radiographed at the X-ray tube voltage of 110 kV, 28% during one rotation, and makes the ratio of the positions 163-3, radiographed at the X-ray tube voltage of 140 kV, 18% during one rotation.

When other conditions in the scan 169 are the same, an amount of information obtained by one rotation increases and noise in acquired data decrease, as the ratio of the number of scanning positions (view count) 163 becomes large.

Then, the scanner unit 103 changes the ratio of the number of scanning positions (view count) 163 according to the X-ray effective energy to perform X-ray irradiation from the X-ray tube assembly 107. The scanner unit 103 takes a radiograph with enlarging the ratio of the number of scanning positions (view count) in the case of radiating X-rays at low effective energy, and takes a radiograph with lessening the ratio of the number of scanning positions in the case of radiating X-rays at high effective energy.

Hence, a difference between numerical values of the SN ratio and CN ratio in respective images (projection data or reconstructed image) becomes small.

In addition, it is desirable to equalize the SN ratio or CN ratio in each image (projection data or reconstructed image) as much as possible by changing the ratio of the number of scanning positions (view count) according to the X-ray effective energy.

In this way, in the thirteenth embodiment, since the scanner unit 103 of the X-ray CT scanner 100 takes a radiograph with enlarging the ratio of the number of scanning positions (view count) in the case of radiating X-rays at low effective energy and takes a radiograph with lessening the ratio of the number of scanning positions (view count) in the case of radiating X-rays at high effective energy, it is possible to lessen the difference between numerical values of the SN ratio and CN ratio in respective images (projection data or reconstructed image) acquired by the multi-energy scan.

In addition, unlike the case of the eleventh and twelfth embodiments, it is not necessary to change an X-ray tube current and scanning speed, in the thirteenth embodiment.

According to this embodiment, by changing the ratio of the view count during one rotation according to the X-ray energy radiated in the X-ray CT scanner, noise volumes in respective energies can be made almost equal.

Embodiment 14

The fourteenth embodiment is an embodiment of being equipped with a target equipped with collision surfaces with different collision angles, and changing the effective energy of X-rays by changing the collision surfaces against which electron rays are made to collide. In addition, although a case that the effective energy is changed is described below as an example, it is also the same as a case that the energy spectrum is changed.

Next, the X-ray CT scanner 100 which relates to the fourteenth embodiment of the present invention will be described using FIGS. 33 to 35.

Figure 33:
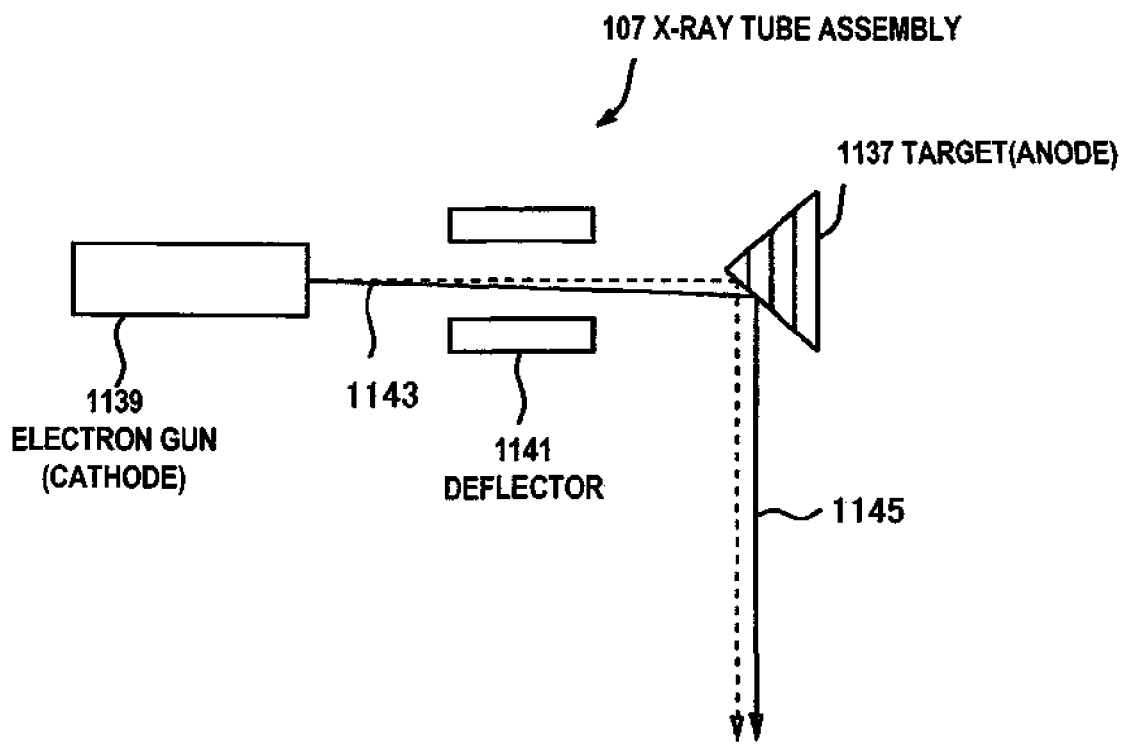
FIG. 33 is a diagram illustrating an X-ray tube assembly 107.

FIG. 33 is a diagram illustrating the X-ray tube assembly 107.

The X-ray tube assembly 107 is equipped with a target (anode) 1137, a deflector 1141, and an electron gun (cathode) 1139. The X-ray tube assembly 107 emits electron rays 1143 from the electron gun 1139, adjusts an angle of the electron rays 1143 with the deflector 1141, and makes them collide against a collision surface 1138 of the target 1137 to make X-rays 1145 generated.

Figure 34:
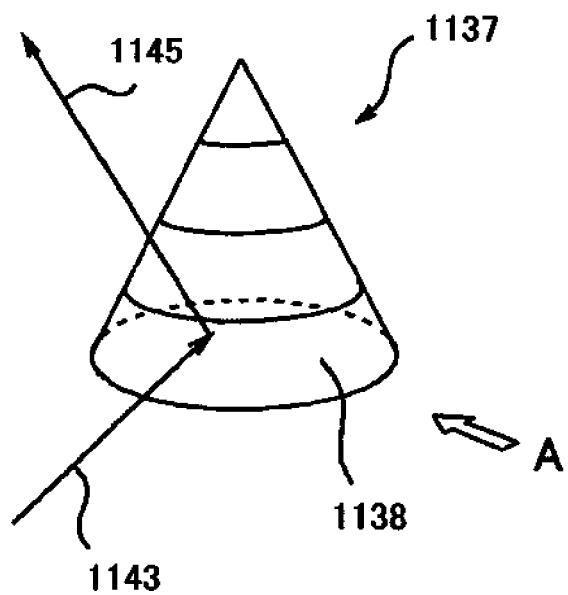
FIG. 34 is a schematic perspective view of a target 1137.

FIG. 34 is a schematic perspective view of the target 1137.

Figure 35:
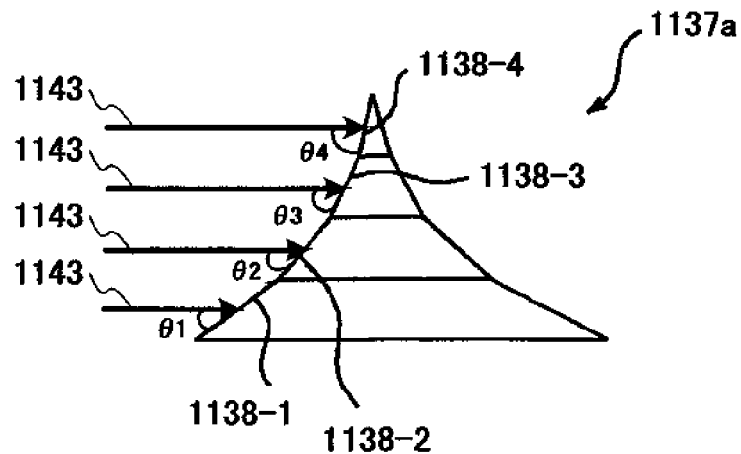
FIG. 35 is a diagram illustrating one aspect (target 1137a) of the target 1137.

FIG. 35 is a diagram illustrating one aspect (target 1137*a*) of the target 1137. FIG. 35 is equivalent to a view illustrated by arrow A in FIG. 34.

The target 1137*a* is equipped with a plurality of collision surfaces 1138-1 to 1138-4. The respective collision surfaces 1138-1 to 1138-4 form different angles (θ1 to θ4) to a traveling direction of the electron rays 1143, respectively.

The effective energy of X-rays 1145 changes with a collision angle (angle to the collision surface 1138 in the traveling direction of the electron rays 1143). The effective energy of X-rays 1145 generated becomes high as the collision angle becomes large, and the effective energy of X-rays 1145 generated becomes low as the collision angle becomes small.

That is, the X-ray tube assembly 107 makes the electron rays 1143 collide with the collision surfaces 1138-1 to 1138-4 of the target 1137*a* to make the X-rays 1145 at different effective energies generated from the respective collision surfaces 1138-1 to 1138-4.

In addition, in order to make the electron rays 1143 selectively collide with the collision surface 1138 at a desired collision angle, a traveling direction of the electron rays 1143 is deflected by the deflector 1141. In this case, for example, a flying focal spot mechanism can be used.

In this way, in the fourteenth embodiment, since the X-ray tube assembly 107 of the X-ray CT scanner 100 is equipped with the target which has the collision surfaces with a plurality of different collision angles, it is possible to generate the X-rays at different effective energies by making electron rays collide with the respective collision surfaces. Moreover, it is possible to change the X-ray effective energy at high speed.

Hence, the X-ray tube assembly 107 of the X-ray CT scanner 100 can radiate a plurality of X-rays, whose effective energies are different, in a multi-energy scan.

In addition, the X-ray tube assembly 107 can change the X-ray effective energy every position (every view), in which scanning is performed, by changing the X-ray effective energy at high speed, and hence, it is possible to perform a multi-energy scan in one scan.

Moreover, since it is possible to construct a target with single material, procurement of a target material is easy.

Furthermore, neither the number of the collision surfaces of a target nor the largeness of collision angles is limited particularly, and hence, two kinds, three kinds, or four or more kinds of collision surfaces may be provided in the target.

According to this embodiment, by radiating electrons from the cathode at different collision angles or in positions where material of target is different, using, for example, a flying focal spot mechanism in the X-ray tube which has a plurality of different target angles, it is possible to radiate the different X-ray energies at high speed.

Embodiment 15

The fifteenth embodiment is an embodiment of changing the X-ray effective energy by constructing a target using a plurality of different material, and changing a site where electron rays are made to collide. In addition, although a case that the effective energy is changed is described below as an example, it is also the same as a case that the energy spectrum is changed.

An X-ray CT scanner 100 which relates to the fifteenth embodiment will be described using FIGS. 36 to 37.

Figure 36:
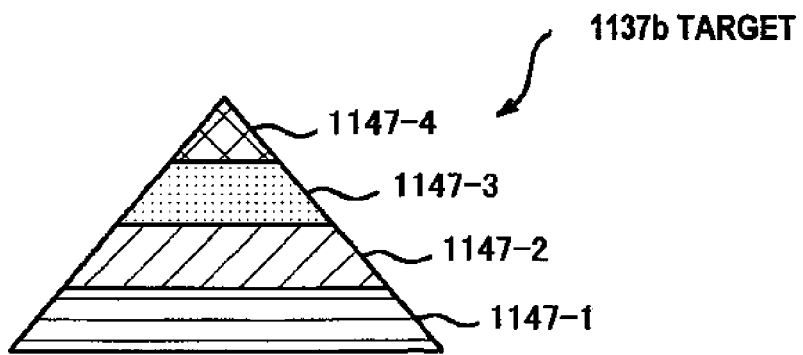
FIG. 36 is a diagram illustrating one aspect (target 1137b) of the target 1137.

FIG. 36 is a diagram illustrating one aspect (target 1137*b*) of the target 1137. FIG. 36 is equivalent to a view illustrated by arrow A in FIG. 34.

The target 1137*b* is constructed of a plurality of target members 1147-1 to 1147-4. Material of the target members 1147-1 to 1147-4 is different, respectively.

Figure 37:
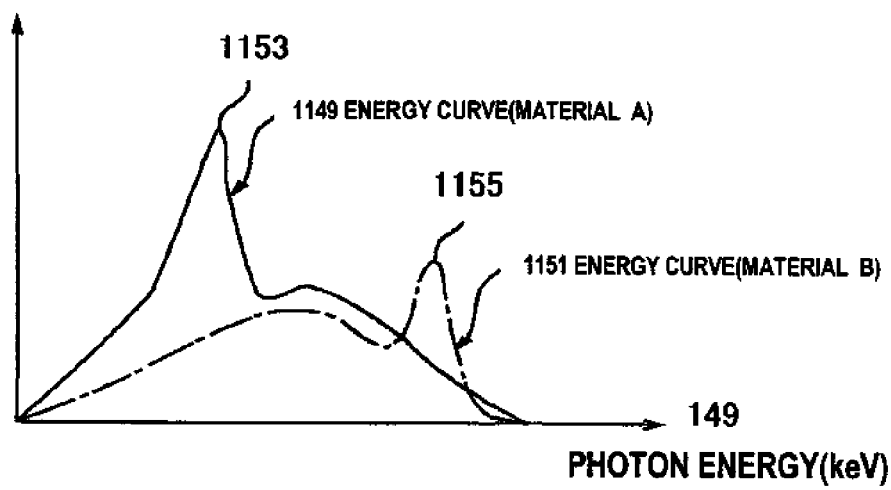
FIG. 37 is a graph illustrating energy distributions of X-rays at the time of using targets whose materials are different.

FIG. 37 is a graph illustrating energy distributions of X-rays at the time of using targets whose material is different.

A horizontal axis denotes the photon energy 149 and a vertical axis denotes the energy intensity 151. In addition, the energy intensity 151 is equivalent to (photon energy)×(photon number).

The energy curve 149 and the energy curve 151 illustrate energy distributions of X-rays 1145 at the time of using material A and material B, which are different, for the target 1137, respectively.

When the material A is used for the target 1137 and the energy curve 1149 is referred to, a characteristic X-ray arises in a position of a point 1153. When the material B is used for the target 1137 and the energy curve 1151 is referred to, a characteristic X-ray arises in a position of a point 1155.

In this way, when the energy intensity of specific photon energy projects and the characteristic X-ray arises, the effective energy of X-rays expresses a value peculiar to material of a target.

For example, when the material of the target is molybdenum, a characteristic X-ray arises at the photon energy of about 20 keV, and when the target material is tungsten, a characteristic X-ray arises at the photon energy of about 70 keV. The value of the X-ray effective energy is shifted toward the energy, where a characteristic X-ray is generated, in comparison with the case that a characteristic X-ray does not arise.

Hence, the effective energy of the X-rays 1145 changes according to the material of the target 1137.

That is, the X-ray tube assembly 107 of the X-ray CT scanner 100 makes the electron rays 1143 collide with the target members 1147-1 to 1147-4 of the target 1137*b* to make the X-rays at different effective energies generated from the respective target members 1147-1 to 1147-4, respectively.

In addition, in order to make the electron rays 1143 selectively collide with the desired target member 1147, a traveling direction of the electron rays 1143 is deflected by a deflector 141. In this case, for example, a flying focal spot mechanism can be used.

In this way, in the fifteenth embodiment, since the X-ray tube assembly 107 of the X-ray CT scanner 100 is equipped with the target which is constructed of a plurality of target members made of different materials, respectively, it is possible to generate the X-rays at different effective energies by making electron rays collide with the respective target members. In addition, it is possible to change the X-ray effective energy at high speed.

Hence, the X-ray tube assembly 107 of the X-ray CT scanner 100 can radiate a plurality of X-rays, whose effective energies are different, in a multi-energy scan.

Furthermore, the X-ray tube assembly 107 can change the X-ray effective energy every position (every view), in which scanning is performed, by changing the X-ray effective energy at high speed, and hence, it is possible to perform a multi-energy scan in one scan.

Moreover, since it is possible to construct a target at a single collision angle, shaping of target members is easy.

In addition, the number of target members and material of a target are not limited particularly, two kinds, three kinds, or four or more kinds of target members may construct the target.

Embodiment 16

The sixteenth embodiment is an embodiment of detecting transmission X-ray by a plurality of X-ray detectors with different sensitivities.

An X-ray CT scanner 100 which relates to the sixteenth embodiment of the present invention will be described using FIG. 38.

Figure 38:
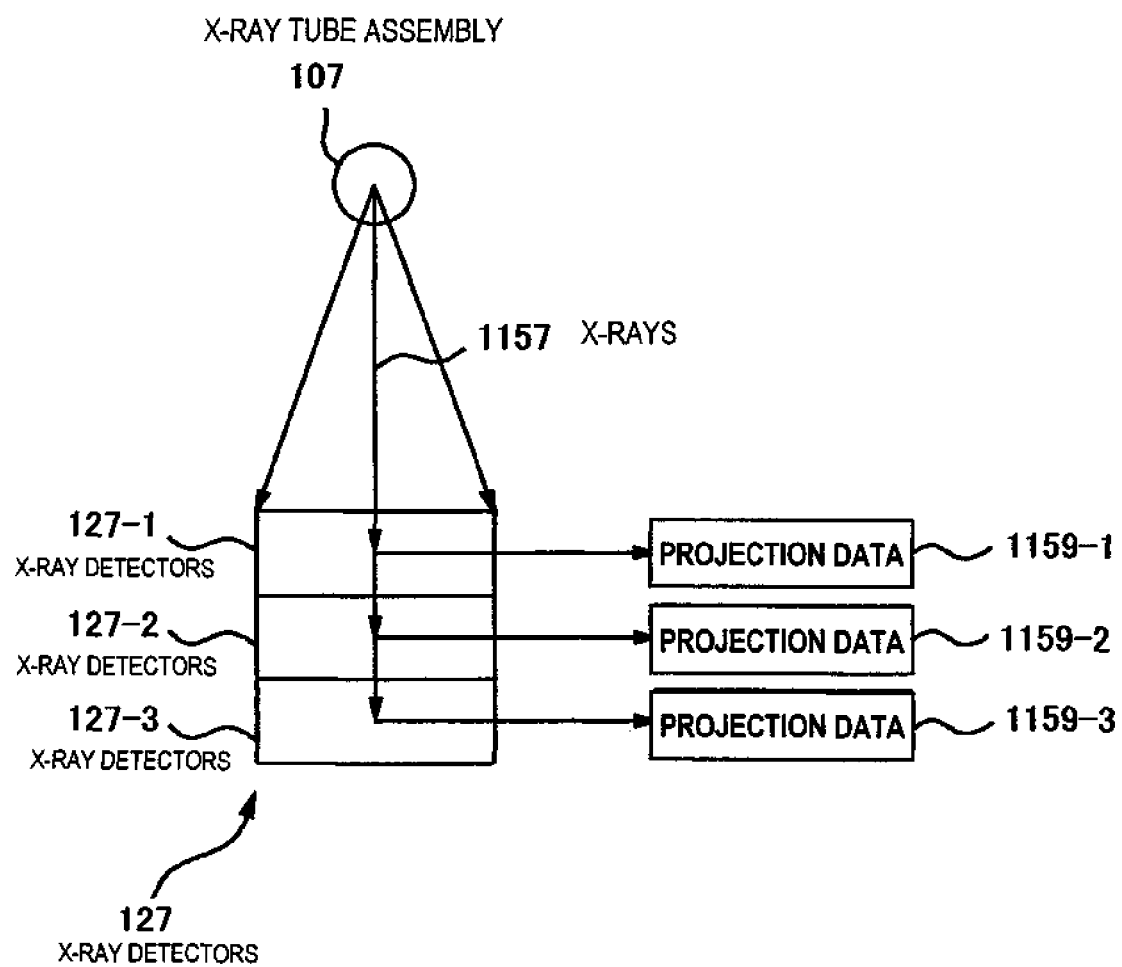
FIG. 38 is a diagram illustrating one aspect of an X-ray detector 127.

FIG. 38 is a diagram illustrating one aspect of the X-ray detector 127.

The X-ray detector 127 is multilayered, and is constructed of a plurality of an X-ray detector 127-1 to an X-ray detector 127-3. The X-ray detector 127-1 to X-ray detector 127-3 have X-ray detecting elements with different sensitivities, respectively. The X-ray detector 127-1 to X-ray detectors 127-3 are X-ray detectors with different sensitivities respectively, such as a solid state detector and a gas sensitive detector, for example.

The X-ray detector 127-1 to X-ray detector 127-3 acquire projection data 1159-1 to projection data 1159-3 with X-rays 1157 with the same effective energy, respectively. Since the sensitivities of the X-ray detector 127-1 to X-ray detector 127-3 are different respectively, the projection data 1159-1 to projection data 1159-3 are equivalent to the projection data acquired with the X-rays with different effective energies, respectively.

In addition, the X-ray detector 127-1 to X-ray detector 127-3 may be multilayered in any direction, such as a radial direction, or circumferential direction, or may be provided separately. Moreover, when multilayering in a direction of a detecting face, they may be arranged by turns. In this case, each element becomes available as a separator mutually. Nevertheless, when taking into consideration suppression of X-ray dosage, and reduction of an amount of exposures, multilayering in the radial direction is desirable.

In this way, in the sixteenth embodiment, the X-ray CT scanner 100 detects the transmission X-ray with a plurality of X-ray detectors with different sensitivities, respectively. Hence, the X-ray CT scanner 100 can acquire image data (projection data or reconstructed images) corresponding to respective X-ray effective energies without changing the X-ray effective energy as if it radiated a plurality of X-rays with different effective energies.

Embodiment 17

The seventeenth embodiment is an embodiment of performing a screen display with matching parameters, affecting an energy spectrum and effective energy, such as a tube voltage, an X-ray tube added filter (hereinafter, only a filter), material of a target, and a collision angle, to the energy spectrum and effective energy.

Figure 39:
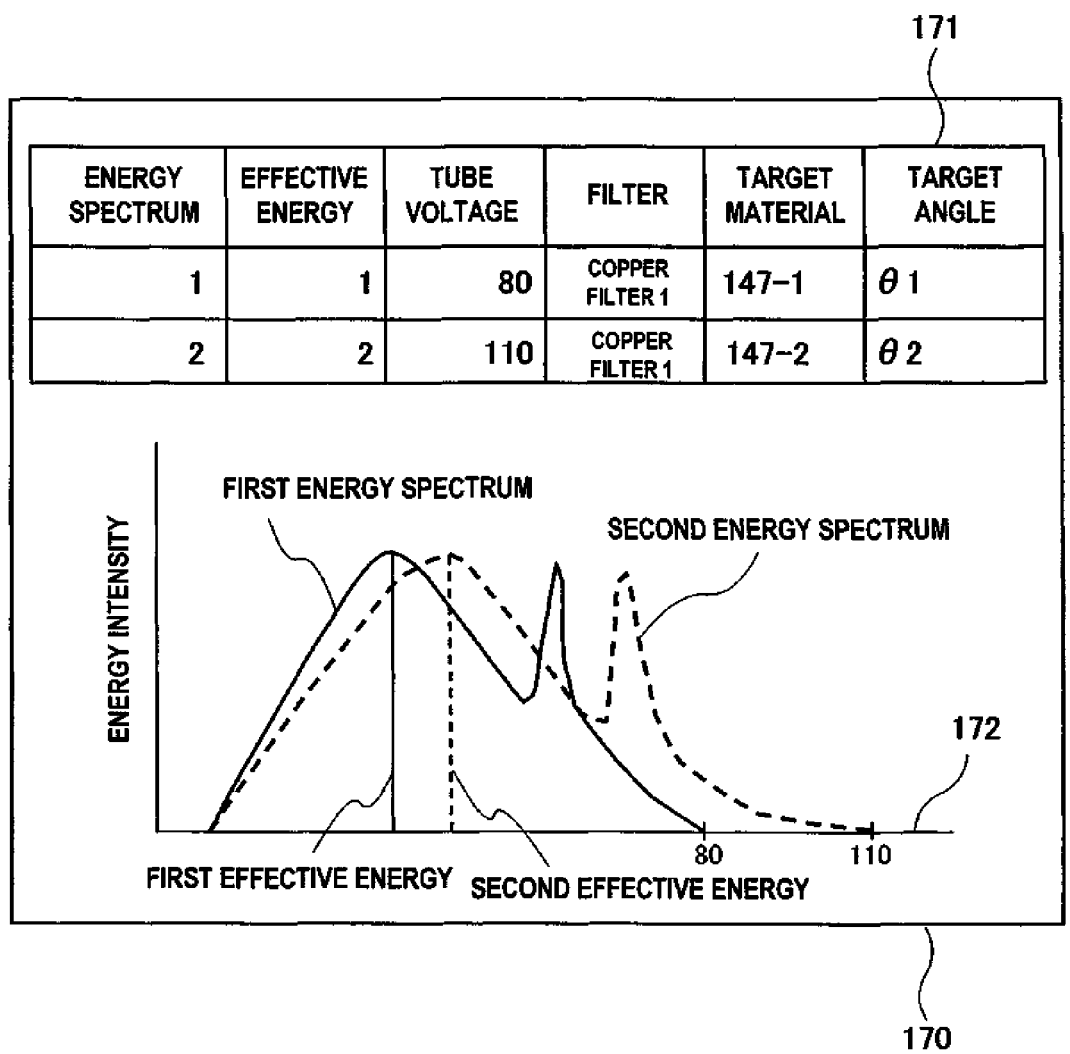
FIG. 39 is a screen display example of a confirmation screen of the parameters, the energy spectrum, and the effective energy.

FIG. 39 shows an example of the screen display of the seventeenth embodiment.

A correspondence table 1671 of an energy spectrum and effective energy, and various parameters is displayed on a screen 170. Although the correspondence table 171 has an "energy spectrum", "effective energy", a "tube voltage", a "filter", "material of a target", and a "collision angle" as a record, what the "energy spectrum" or "effective energy" is matched to at least one of the "tube voltage", "filter", "material of a target", and "collision angles" may be also used. The energy spectrum or effective energy at the time of changing the above-mentioned parameters may be distinguished only by performing labeling as illustrated in the correspondence table 171.

Furthermore, a graph 172 may be displayed on the screen 170 and shapes of the above-mentioned first energy spectrum and second energy spectrum, and the first effective energy and second effective energy may be illustrated.

In addition, when a parameter is input into the correspondence table 171 on the screen 170, the X-ray tube assembly 107 may be able to be controlled according to the input parameter.

According to this embodiment, it is possible to perform confirmation with matching the parameters to the energy spectrum, or effective energy.

As mentioned above, although suitable embodiments, such as the X-ray CT scanners which relate to the present invention, are described with referring to accompanying drawings, the present invention is not limited to these examples. It is apparent that those skilled in the art can conceive various kinds of modified examples or corrected examples within a technical idea disclosed in the present application, and it is understood that they also naturally belong to the technical scope of the present invention.

In addition, in the above-described embodiment, although the X-ray CT scanner is used, it is not limited to this, but can be applied also to a CT scanner and an X-ray radiographing apparatus using a neutron beam, a positron, a gamma-ray, or light.

Moreover, although the general X-ray CT scanner which has one set of X-ray tube and X-ray detector is used in this embodiment, it is applicable also to a multi-tube CT scanner having two or more sets of X-ray tube and X-ray detector.

INDUSTRIAL APPLICABILITY

The above-described radiographing apparatus and image processing program are applicable not only to a medical object but also other industrial objects so long as it is a radiographing apparatus which radiographs internal structure of an object noninvasively using a plurality of X-rays which have different energy spectra.

The invention claimed is:

1. A radiographing apparatus which comprises:
an X-ray source which radiates x-rays with a first energy spectrum and x-rays with a second energy spectrum;
an X-ray detector which detects the x-rays with the first energy spectrum and the x-rays with the second energy spectrum transmitted through an object to be examined, and outputs projection data of the first energy spectrum and projection data of the second energy spectrum;
a control device which controls operations of the X-ray source and the X-ray detector;
an image processing device which generates a desired image on the basis of the projection data of the first energy spectrum and the projection data of the second energy spectrum; and
a display device which displays the image, wherein the image processing device comprises:
an acquisition device which acquires the projection data of the first energy spectrum and the projection data of the second energy spectrum;
a synthetic image generating device which synthesizes a first image on the basis of the projection data of the first energy spectrum and a second image on the basis of the projection data of the second energy spectrum according to a predetermined synthetic condition to generate a synthetic image,
wherein the display device displays the generated synthetic image; and
a correction device which performs correction according to levels of effective energy of the first energy spectrum and effective energy of the second energy spectrum in order to equalize noise of the first image to noise of the second image for the first image based on projection data of the first energy spectrum and the second image based on projection data of the second energy spectrum,
wherein the synthetic image generating device synthesizes the first image and the second image with noise equalized by the correction device.

2. The radiographing apparatus according to claim 1, wherein
the image processing device generates a first reconstructed image by reconstructing projection data of the first energy spectrum, and generates a second reconstructed image by reconstructing projection data of a second energy spectrum, and
the synthetic image generating device synthesizes the first reconstructed image and the second reconstructed image according to the predetermined synthetic condition to generate the synthetic image.

3. The radiographing apparatus according to claim 2, further comprising:
a mixed ratio calculation device which calculates a mixed ratio of the first reconstructed image and the second reconstructed image, wherein
the synthetic image generating device synthesizes the first reconstructed image and the second reconstructed image according to the mixed ratio which the mixed ratio calculation device calculates.

4. The radiographing apparatus according to claim 3, wherein
the mixed ratio calculation device changes the mixed ratio for every pixel in the first reconstructed image and the second reconstructed image or for every first local area set in the first reconstructed image and second local area set in an area equivalent to the first local area in the second reconstructed image according to local physical quantity.

5. The radiographing apparatus according to claim 3, wherein
the mixed ratio calculation device identifies tissue with the same vital function in the first reconstructed image and in the second reconstructed image, and determines a mixed ratio for said tissue on the basis of a first energy difference and a second energy difference, where the first energy difference is an energy difference between an X-ray absorption edge of the tissue and effective energy of the first energy spectrum, and the second energy difference is an energy difference between the X-ray absorption edge of the tissue and effective energy of the second energy spectrum.

6. The radiographing apparatus according to claim 2, wherein
the synthetic image generating device assigns different colors respectively to the first reconstructed image and the second reconstructed image to generate a plurality of monochrome color images, and synthesizes a plurality of monochrome color images to generate a synthetic color image.

7. The radiographing apparatus according to claim 6, wherein the synthetic image generating device uses colors selected from blue, green and red as the different colors.

8. The radiographing apparatus according to claim 6, further comprising:
a mixed ratio calculation device which calculates a mixed ratio of the plurality of monochrome color images, wherein
the synthetic image generating device synthesizes the plurality of monochrome color images according to the calculated mixed ratio.

9. The radiographing apparatus according to claim 1, wherein
the synthetic image generating device synthesizes projection data of the first energy spectrum and projection data of the second energy spectrum according to the predetermined synthetic condition to generate synthetic projection data, and reconstructs the synthesized projection data to generate the synthetic image.

10. The radiographing apparatus according to claim 9, wherein
the synthetic image generating device combines projection data of the first energy spectrum and projection data of the second energy spectrum which correspond to a position of the object to generate combined projection data, and reconstructs the combined projection data to generate the synthetic image.

11. The radiographing apparatus according to claim 1, further comprising:
a correction device which performs correction according to levels of effective energy of the first energy spectrum and effective energy of the second energy spectrum in order to smooth noise of the first image and noise of the second image for the first image based on projection data of the first energy spectrum and the second image based on projection data of the second energy spectrum, wherein
the synthetic image generating device synthesizes the first image and the second image that the noise is smoothed by the correction device.

12. The radiographing apparatus according to claim 11, wherein the correction device is a device which adjusts at least one of image filter size, scanning speed, a tube current, and an X-ray irradiation range during scanning.

13. The radiographing apparatus according to claim 1, wherein
the X-ray source comprises a target which has a plurality of collision surfaces with different collision angles respectively, and an electron ray generation device which makes electron rays collide with the target, and performs variable control of an energy spectrum or effective energy of X-rays radiated from the X-ray source by making electron rays collide with collision surfaces of a target at different collision angles, or with a target which is constructed of a plurality of target members of different material, and performs variable control of an energy spectrum or effective energy of X-rays radiated from the X-ray source by making the electron rays collide with the target with different material.

14. The radiographing apparatus according to claim 1, further comprising:
an X-ray display device which associates (a) least one of a tube voltage applied to the X-ray source, an X-ray tube filter with which the X-ray source is equipped, which filter absorbs a part of X-rays radiated from a target with which electron rays collide, a collision angle of a collision surface with which the electron rays are made to collide, and a target member with which the electron rays are made to collide, and (b) an energy spectrum or effective energy of X-rays radiated from the X-ray source, wherein the display device displays information related to the energy spectrum or effective energy corresponding thereto.

15. The radiographing apparatus according to claim 1, wherein the X-ray detector comprises a plurality of X-ray detectors with respective different sensitivities.

16. A radiographing apparatus which comprises:
an X-ray source which radiates x-rays with a first energy spectrum and x-rays with a second energy spectrum;
an X-ray detector which detects the x-rays with the first energy spectrum and the x-rays with the second energy spectrum transmitted through an object to be examined, and outputs projection data of the first energy spectrum and projection data of the second energy spectrum;
a control device which controls operations of the X-ray source and the X-ray detector;
an image processing device which generates a desired image on the basis of the projection data of the first energy spectrum and the projection data of the second energy spectrum; and
a display device which displays the image,
wherein the image processing device comprises:
an acquisition device which acquires the projection data of the first energy spectrum and the projection data of the second energy spectrum;
a synthetic image generating device which synthesizes a first image on the basis of the projection data of the first energy spectrum and a second image on the basis of the projection data of the second energy spectrum according to a predetermined synthetic condition to generate a synthetic image,
wherein the display device displays the generated synthetic image;
wherein the image processing device generates a first reconstructed image by reconstructing projection data of the first energy spectrum, and a second reconstructed image by reconstructing projection data of a second energy spectrum, and
the synthetic image generating device synthesizes the first reconstructed image and the second reconstructed image according to the predetermined synthetic condition to generate the synthetic image; and
wherein the synthetic image generating device generates a differential synthetic color image by generating an average value image of the first reconstructed image and the second reconstructed image, calculating a first difference image related to a difference between the average value image and the first reconstructed image, and a second difference image related to a difference between the average value image and the second reconstructed image respectively, and assigning different colors to the first difference image and the second difference image respectively, generating a plurality of differential monochrome color images, and synthesizing the plurality of differential monochrome color images.

17. The radiographing apparatus according to claim 16, wherein
the synthetic image generating device generates an average value image of the first reconstructed image and the second reconstructed image, calculates a first difference image related to a difference between the average value image and the first reconstructed image and a second difference image related to a difference between the average value image and the second reconstructed image respectively, and generates an emphasis image containing pixel values related to respective pixels of the difference images having the greatest absolute values.

18. A radiographing apparatus which comprises:
an X-ray source which radiates x-rays with a first energy spectrum and x-rays with a second energy spectrum;
an X-ray detector which detects the x-rays with the first energy spectrum and the x-rays with the second energy spectrum transmitted through an object to be examined, and outputs projection data of the first energy spectrum and projection data of the second energy spectrum;
a control device which controls operations of the X-ray source and the X-ray detector;
an image processing device which generates a desired image on the basis of the projection data of the first energy spectrum and the projection data of the second energy spectrum; and
a display device which displays the image,
wherein the image processing device comprises:
an acquisition device which acquires the projection data of the first energy spectrum and the projection data of the second energy spectrum;
a synthetic image generating device which synthesizes a first image on the basis of the projection data of the first energy spectrum and a second image on the basis of the projection data of the second energy spectrum according to a predetermined synthetic condition to generate a synthetic image,
wherein the display device displays the generated synthetic image; and
an interpolation device which performs interpolation processing on the basis of projection data of the first energy spectrum and projection data of the second energy spectrum, and generates projection data of an energy spectrum different from the first energy spectrum and the second energy spectrum, wherein
the image processing device reconstructs projection data, generated by the interpolation device, to generate a reconstructed image corresponding to the different energy spectrum.

19. An image processing program stored in non-transitory form in a computer-readable medium, said program when executed in a computer causing the carrying out of the following steps:
a reading step of reading projection data of an X-ray with a first energy spectrum and projection data of an X-ray with a second energy spectrum which transmit an object to be examined; and
a synthesizing step of synthesizing a first image on the basis of the projection data of the first energy spectrum, and a second image on the basis of the projection data of the second energy spectrum according to a predetermined synthetic condition, and generating a synthetic image;
a correction step which performs correction according to levels of effective energy of the first energy spectrum and effective energy of the second energy spectrum in order to equalize noise of the first image to noise of the second image for the first image based on projection data of the first energy spectrum and the second image based on projection data of the second energy spectrum,
wherein noise in the synthetic image is equalized by said correction step.

20. The image processing program according to claim 19, wherein
the synthesizing step combines projection data of a first energy spectrum and projection data of the second energy spectrum which correspond to respective positions in the object to generate combined projection data, and reconstructs the combined projection data to generate a synthetic image.

* * * * *